United States Patent
Isoda et al.

(10) Patent No.: US 9,972,087 B2
(45) Date of Patent: May 15, 2018

(54) BIOLOGICAL SUBSTANCE QUANTITATIVE DETERMINATION METHOD, IMAGE PROCESSING DEVICE, PATHOLOGICAL DIAGNOSIS SUPPORT SYSTEM, AND COMPUTER READABLE MEDIUM

(71) Applicant: KONICA MINOLTA, INC., Chiyoda-ku (JP)

(72) Inventors: Takeshi Isoda, Sayama (JP); Naoko Furusawa, Hino (JP); Yasuhiro Watanabe, Chiyoda-ku (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days. days.

(21) Appl. No.: 15/325,355

(22) PCT Filed: Jul. 11, 2014

(86) PCT No.: PCT/JP2014/068569
§ 371 (c)(1),
(2) Date: Jan. 10, 2017

(87) PCT Pub. No.: WO2016/006096
PCT Pub. Date: Jan. 14, 2016

(65) Prior Publication Data
US 2017/0186156 A1 Jun. 29, 2017

(51) Int. Cl.
*G06K 9/00* (2006.01)
*G06T 7/00* (2017.01)
(Continued)

(52) U.S. Cl.
CPC ............ *G06T 7/0012* (2013.01); *G01N 1/30* (2013.01); *G01N 21/6428* (2013.01);
(Continued)

(58) Field of Classification Search
None
See application file for complete search history.

(56) References Cited

U.S. PATENT DOCUMENTS

2013/0161536 A1   6/2013   Hasegawa
2013/0230866 A1   9/2013   Miyashita et al.

FOREIGN PATENT DOCUMENTS

JP   2013-57631   3/2013
JP   2013-88296   5/2013
(Continued)

OTHER PUBLICATIONS

International Preliminary Report on Patentability dated Jan. 17, 2017 and the Written Opinion of the International Searching Authority dated Oct. 21, 2014 which issued in the corresponding International Patent Application No. PCT/JP2014/068569.

*Primary Examiner* — Atiba O Fitzpatrick
(74) *Attorney, Agent, or Firm* — Cozen O'Connor

(57) ABSTRACT

A quantitative determination method of a biological substance in a sample stained with a staining reagent comprising fluorescent particles each encapsulating a fluorescent substance and binding to a biological substance recognizing site. The method comprises inputting a fluorescent image obtained by photographing the sample, extracting a predetermined region from the fluorescent image to calculate an integrated luminance of the predetermined region, and counting the number of fluorescent particles contained in the predetermined region from the integrated luminance and the average luminance per fluorescent particle. The average luminance per fluorescent particle is calculated from a correlation between the number of fluorescent particles counted from an image of the fluorescent particles visualized and the luminance derived from fluorescent light from the fluorescent particles and calculated from a fluorescent image (Continued)

of a region identical to the region taken in the image from which the number of fluorescent particles is counted.

16 Claims, 11 Drawing Sheets

(51) Int. Cl.
    *G01N 21/64*     (2006.01)
    *G01N 1/30*     (2006.01)
    *G01N 33/543*     (2006.01)
    *G06T 7/90*     (2017.01)

(52) U.S. Cl.
    CPC ......... *G01N 33/54313* (2013.01); *G06T 7/90* (2017.01); *G01N 2021/6439* (2013.01); *G06T 2207/10064* (2013.01)

(56) References Cited

FOREIGN PATENT DOCUMENTS

| WO | WO 2012/029342 | 3/2012 |
| WO | WO 2012/029752 | 3/2012 |
| WO | WO 2012/124763 | 9/2012 |
| WO | WO 2013/035703 | 3/2013 |
| WO | WO 2013/146694 | 10/2013 |

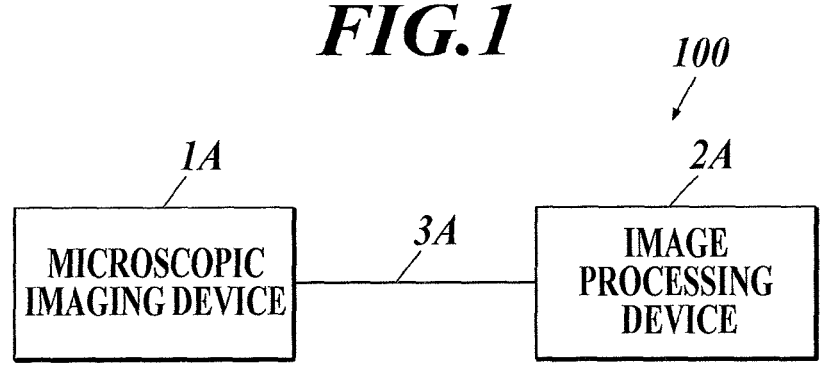
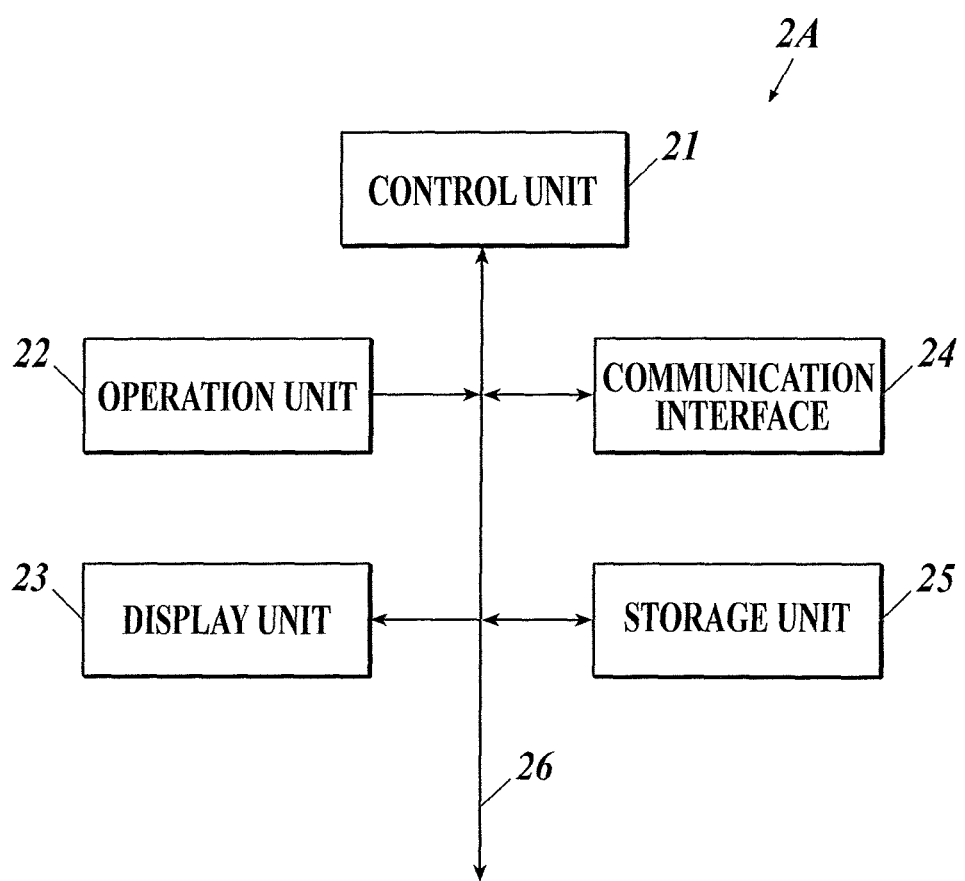

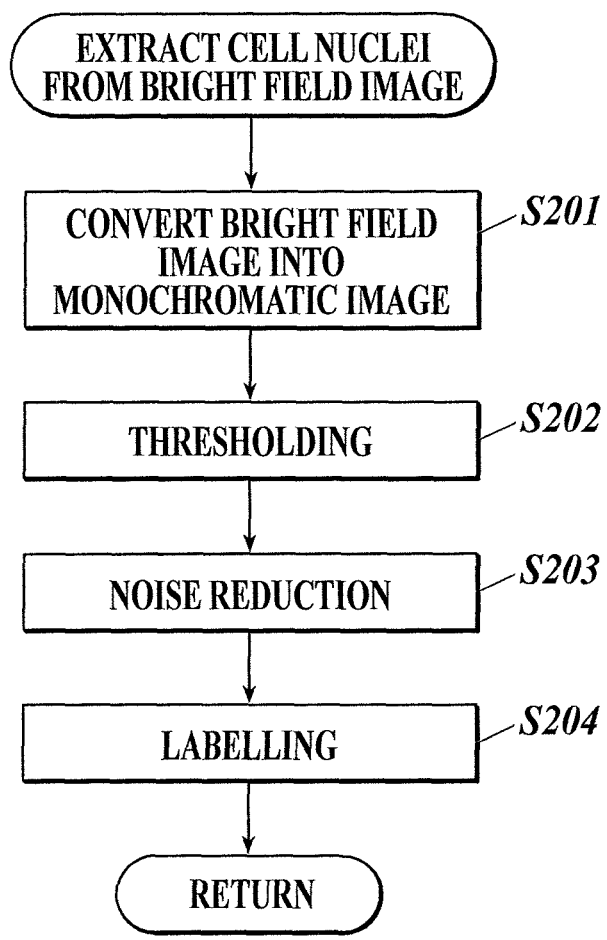

| | | | | | | | COORDINATE X | | | | | | | | | | | |
|---|---|---|---|---|---|---|---|---|---|---|---|---|---|---|---|---|---|---|
| | | 37 | 26 | 64 | | | | | | | | 62 | 63 | 13 | | | | |
| | | 59 | 31 | 59 | 69 | | | | | | 41 | 56 | 43 | 40 | 65 | | | |
| | | 34 | 69 | 59 | 34 | 45 | 22 | 50 | 77 | 57 | 68 | 55 | 68 | 69 | 42 | 51 | 63 | |
| | | | 42 | 59 | 33 | 38 | 37 | 66 | 78 | 53 | 90 | 89 | 92 | 83 | 43 | 74 | 75 | |
| | | | 29 | 8 | 24 | 46 | 22 | 54 | 65 | 40 | 105 | 81 | 120 | 75 | 72 | 77 | 58 | |
| COORDINATE Y | | | 35 | 13 | 27 | 52 | 6 | 26 | 95 | 129 | 124 | 88 | 108 | 123 | 101 | 64 | 84 | |
| | | | 45 | 4 | 38 | 19 | 31 | 131 | 212 | 311 | 290 | 182 | 79 | 76 | 86 | 82 | 62 | |
| | | | 37 | 29 | 15 | 10 | 58 | 278 | 538 | 680 | 518 | 319 | 116 | 80 | 88 | 82 | 62 | |
| | 53 | 55 | 31 | 26 | 33 | 69 | 124 | 374 | 701 | 823 | 782 | 398 | 155 | 84 | 92 | 88 | 42 | |
| | 42 | 62 | 25 | 53 | 51 | 36 | 135 | 393 | 577 | 740 | 561 | 335 | 131 | 112 | 97 | 72 | 48 | 89 |
| | 44 | 41 | 23 | 45 | 42 | 76 | 115 | 256 | 390 | 481 | 341 | 160 | 101 | 72 | 86 | 66 | 75 | 91 |
| | | | 28 | 36 | 55 | 87 | 120 | 159 | 156 | 211 | 135 | 147 | 90 | 64 | 69 | | | |
| | | | 22 | 64 | 58 | 62 | 82 | 103 | 122 | 137 | 111 | 109 | 105 | 108 | 91 | | | |
| | | | 77 | 73 | 49 | 55 | 81 | 101 | 96 | 117 | 114 | 109 | | | | | | |
| | | | 42 | 39 | 52 | 49 | 45 | 80 | 90 | 69 | 98 | 104 | | | | | | |
| | | | 26 | 47 | 35 | 35 | 88 | | | | | | | | | | | |
| | | | | | | | | | | | | | | | | | | |

BIOLOGICAL SUBSTANCE QUANTITATIVE DETERMINATION METHOD, IMAGE PROCESSING DEVICE, PATHOLOGICAL DIAGNOSIS SUPPORT SYSTEM, AND COMPUTER READABLE MEDIUM

RELATED APPLICATIONS

This is a U.S. National Phase Application under 35 USC 371 of International Application PCT/JP2014/068569 filed on Jul. 11, 2014.

TECHNICAL FIELD

The present invention relates to a quantitative determination method of a biological substance using information on the luminance of a fluorescent substance, an image processing device, a pathological diagnosis support system, and a program.

BACKGROUND

With recent expansion of therapies using molecular target drugs, typically antibody drugs, quantitative determination of a biological substance (antigen) on target cells has been required for more effective design of molecular target drugs. A known method for detecting a biological substance is tissue analysis based on binding of a fluorescent substance having a biological substance recognizing site and a biological substance reactive to the biological substance recognizing site.

Patent Literature 1 proposes a method of staining a tissue with a phosphor having a biological substance recognizing site, and determining the number of fluorescent bright spots and the intensity of fluorescent light from the average luminance per particle calculated through analysis of peaks in the luminance distribution of the fluorescent bright spots to evaluate the expression level of the biological substance.

PRIOR ART DOCUMENTS

Patent Documents

Patent document 1: Japanese Patent Application Laid-Open No. 2013-57631

SUMMARY OF THE INVENTION

Problems to be Solved by the Invention

Since the conventional method according to Patent Literature 1 involving analysis of the peaks in the luminance distribution of the fluorescent bright spots calculates the average luminance per phosphor particle serving as a reference from a photographed fluorescent image, the average luminance cannot be calculated accurately when phosphor particles which are close to each other form clusters. The luminance determined from the fluorescent image contains not only the luminance of the phosphor but also background noises, such as autofluorescence. These background noises readily cause errors in the luminance serving as the reference, obstructing accurate quantitative determination of the biological substance.

An object of the present invention is to provide a quantitative determination method of a biological substance that enables accurate determination of the number of specific biological substances in a sample, an image processing device, a pathological diagnosis support system, and a program.

Means to Solve the Problems

According to the first aspect of the present invention, there is provided a quantitative determination method of a biological substance in a sample stained with a staining reagent including fluorescent particles each encapsulating a fluorescent substance and binding to a biological substance recognizing site, the method including:

an inputting step of inputting a fluorescent image obtained by photographing the sample, a first calculating step of extracting a predetermined region from the fluorescent image to calculate an integrated luminance of the predetermined region, and a second calculating step of counting the number of fluorescent particles included in the predetermined region from the integrated luminance and the average luminance per fluorescent particle, wherein the average luminance per fluorescent particle is calculated from a correlation between the number of fluorescent particles counted from an image of the fluorescent particles visualized and the luminance derived from fluorescent light from the fluorescent particles and calculated from a fluorescent image of a region identical to the region taken in the image from which the number of fluorescent particles is counted.

According to the second embodiment of the present invention, there is provided a quantitative determination method of a biological substance according to the first embodiment, wherein calculation of the average luminance per fluorescent particle includes:

a step of extracting bright spot regions from a fluorescent image obtained by photographing the fluorescent particles, the bright spot regions being derived from fluorescent light from the fluorescent particles, a step of calculating a luminance of bright spots through integration of luminances of the bright spot regions, a step of counting the number of fluorescent particles included in each of the bright spot regions with a scanning electron microscope, and a step of calculating the average luminance from a correlation between the luminance of bright spots and the number of fluorescent particles included in each of the bright spot regions.

According to the third embodiment of the present invention, there is provided the quantitative determination method of a biological substance according to first or second embodiment, wherein the fluorescent particles have an average particle size of 40 nm or more and 280 nm or less.

According to the fourth embodiment of the present invention, there is provided the quantitative determination method of a biological substance according to any one of first to third embodiments, wherein the fluorescent particles include melamine.

According to the fifth embodiment of the present invention, there is provided the quantitative determination method of a biological substance according to any one of first to fourth embodiments, wherein the biological substance is a HER2 protein or Ki67 protein.

According to the sixth embodiment of the present invention, there is provided the quantitative determination method of a biological substance according to any one of first to fifth embodiments, further including a step of calibrating the average luminance per fluorescent particle.

According to the seventh embodiment of the present invention, there is provided an image processing device for quantitative determination of a biological substance in a sample stained with a staining reagent including fluorescent particles each encapsulating a fluorescent substance and binding to a biological substance recognizing site, the device including:

an input unit inputting a fluorescent image obtained by photographing the sample, a first calculating unit of extracting a predetermined region from the fluorescent image to calculate an integrated luminance of the predetermined region, and a second calculating unit of counting the number of fluorescent particles included in the predetermined region from the integrated luminance and the average luminance per fluorescent particle, wherein the average luminance per fluorescent particle is calculated from a correlation between the number of fluorescent particles counted from an image of the fluorescent particles visualized and the luminance derived from fluorescent light from the fluorescent particles and calculated from a fluorescent image of a region identical to the region taken in the image from which the number of fluorescent particles is counted.

According to the eighth embodiment of the present invention, there is provided a pathological diagnosis support system, including:

the image processing device, and an imaging device acquiring the fluorescent image to be used in the image processing device.

According to the ninth embodiment of the present invention, there is provided a program for quantitative determination of a biological substance in a sample stained with a staining reagent including fluorescent particles each encapsulating a fluorescent substance and binding to a biological substance recognizing site, the program causing a computer to function as:

an input unit inputting a fluorescent image obtained by photographing the sample, a first calculating unit of extracting a predetermined region from the fluorescent image to calculate an integrated luminance of the predetermined region, and a second calculating unit of counting the number of fluorescent particles included in the predetermined region from the integrated luminance and the average luminance per fluorescent particle, wherein the average luminance per fluorescent particle is calculated from a correlation between the number of fluorescent particles counted from an image of the fluorescent particles visualized and the luminance derived from fluorescent light from the fluorescent particles and calculated from a fluorescent image of a region identical to the region taken in the image from which the number of fluorescent particles is counted.

Effects of the Invention

The present invention can quantitatively determine the exact number of specific biological substances in a sample.

BRIEF DESCRIPTION OF THE DRAWINGS

FIG. 1 is a diagram illustrating a configuration of a pathological diagnosis support system using the quantitative determination method of a biological substance of the present invention.

FIG. 2 is a block diagram illustrating a functional configuration of the image processing device in FIG. 1.

FIG. 6 is a flowchart illustrating the detailed processes in Step S2 of FIG. 5.

EMBODIMENTS TO CARRY OUT THE INVENTION

Figure 3:
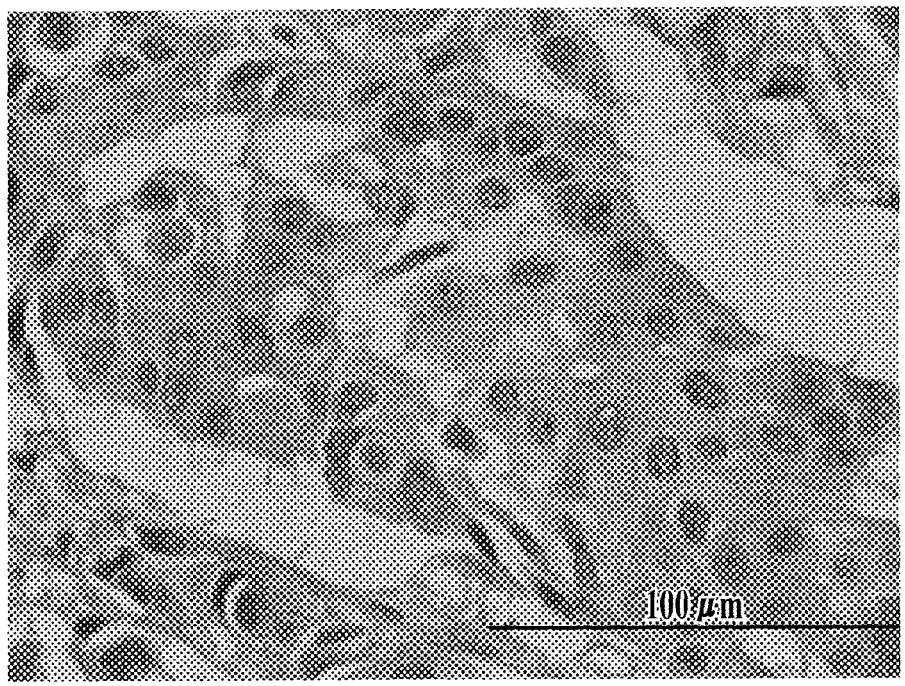
FIG. 3 is a diagram illustrating an exemplary bright field image.

Embodiments for implementing the present invention will now be described with reference to the attached drawings, which should not be construed to limit the present invention.

<Configuration of Pathological Diagnosis Support System 100>

FIG. 1 illustrates an example of overall configuration of the pathological diagnosis support system 100 that employs the quantitative determination method of a biological substance according to the present invention. The pathological diagnosis support system 100 acquires a microscopic image of a target tissue sample stained with a predetermined staining reagent, analyzes the acquired microscopic image, and outputs a feature quantity that quantitatively represents expression of a specific biological substance in the target tissue sample.

As illustrated in FIG. 1, the pathological diagnosis support system 100 includes a microscopic imaging device 1A, an image processing device 2A, and an interface, such as a cable 3A, connecting the microscopic imaging device 1A and the image processing device 2A for transmission and reception of data. The microscopic imaging device 1A may be connected to the image processing device 2A in any manner. For example, the microscopic imaging device 1A and the image processing device 2A may be connected through a local area network (LAN) or wireless communication.

The microscopic imaging device 1A is a known optical microscope provided with a camera, which acquires a microscopic image of a tissue sample on a microscopic slide fixed on a slide stage, and transmits the microscopic image to the image processing device 2A.

The microscopic imaging device 1A includes an irradiator, a focusing unit, a photographing unit, and a communication interface (I/F). The irradiator includes a light source and a filter, and emits light toward the tissue sample on the microscopic slide placed on the slide stage. The focusing unit includes an eyepiece lens and an object lens. The focusing unit focuses transmitted light, reflected light, or fluorescent light, which is emitted from the tissue sample on the microscopic slide in response to the irradiated light, into an image. The photographing unit includes a charge coupled device (CCD) sensor. The photographing unit is specifically a camera disposed in a microscope to photograph an image formed by the focusing unit, and produce the digital image data of the microscopic image. The communication interface transmits the image data of the microscopic image to the image processing device 2A. The microscopic imaging device 1A in the present embodiment includes a bright field unit suitable for bright field microscopy composed of a combination of an irradiating subunit and a focusing subunit, and a fluorescence unit suitable for fluorescent microscopy composed of a combination of an irradiating subunit and a focusing subunit, and can switch between these subunits, i.e., between bright field microscopy and fluorescent microscopy.

Besides the microscope provided with a camera, the microscopic imaging device 1A may be any device, for example, a virtual microscopic slide preparing device that scans a microscopic slide fixed on a stage of a microscope to acquire a microscopic image of an overall tissue sample (see Japanese Publication of International Patent Application No. 2002-514319, for example). The virtual microscopic slide preparing device can acquire image data of the overall tissue sample that can be displayed on a display unit at once.

The image processing device 2A analyzes the microscopic image transmitted from the microscopic imaging device 1A to calculate the distribution of the expression of the specific biological substance in the target tissue sample.

FIG. 2 illustrates an exemplary functional configuration of the image processing device 2A. As illustrated in FIG. 2, the image processing device 2A includes a control unit 21, an operating unit 22, a display unit 23, a communication interface (I/F) 24, and a storage unit 25, which are connected to each other through a bus 26.

The control unit 21 includes a central processing unit (CPU), and a random access memory (RAM). The control unit 21 executes multiple processes in cooperation with a variety of programs stored in the storage unit 25 to control the overall operation of the image processing device 2A. For example, the control unit 21 executes image analysis in cooperation with a program stored in the storage unit 25 (see FIG. 5) to implement a function as a unit executing a step of inputting a fluorescent image, a first calculating step, and a second calculating step.

The operating unit 22 includes a keyboard including keys for inputting characters and numbers and several functional keys, and a pointing device, such as a mouse. The operating unit 22 outputs input signals to the control unit 21, i.e., signals generated by press of keys on the keyboard and by operation of the mouse.

The display unit 23 includes a monitor, such as a cathode ray tube (CRT) display or a liquid crystal display (LCD). The display unit 23 displays a variety of windows in response to display signals input from the control unit 21. The display unit 23 in the present embodiment functions as an output unit for outputting the results of image analysis.

The communication interface 24 allows data transmission and reception between the microscopic imaging device 1A and external devices, such as the microscopic imaging device 1A. The communication interface 24 functions as a unit for inputting a bright field image and a fluorescent image.

The storage unit 25 includes a hard disk drive (HDD) or a nonvolatile memory composed of a semiconductor, for example. The storage unit 25 stores a variety of programs and data as described above.

Besides, the image processing device 2A may include a LAN adaptor and a router to be connected to external apparatuses through a communication network, such as a LAN.

The image processing device 2A in the present embodiment preferably analyzes the sample using the bright field image and fluorescent image transmitted from the microscopic imaging device 1A.

The bright field image is a microscopic image of a tissue sample stained with a haematoxylin (H) staining reagent or a haematoxylin-eosin (HE) staining reagent taken in the bright field with the microscopic imaging device 1A. This image represents the morphology of cells in the tissue sample. The haematoxylin is a blue violet dye for staining basophilic tissues, such as cell nuclei, bone tissues, part of cartilaginous tissues, and serum components. The eosin is a red to pink color dye for staining acidophilic tissues, such as cytoplasms, connective tissues of soft tissues, erythrocytes, fibrin, and endocrine granules. FIG. 3 illustrates an exemplary bright field image of an HE-stained tissue sample.

Figure 4:
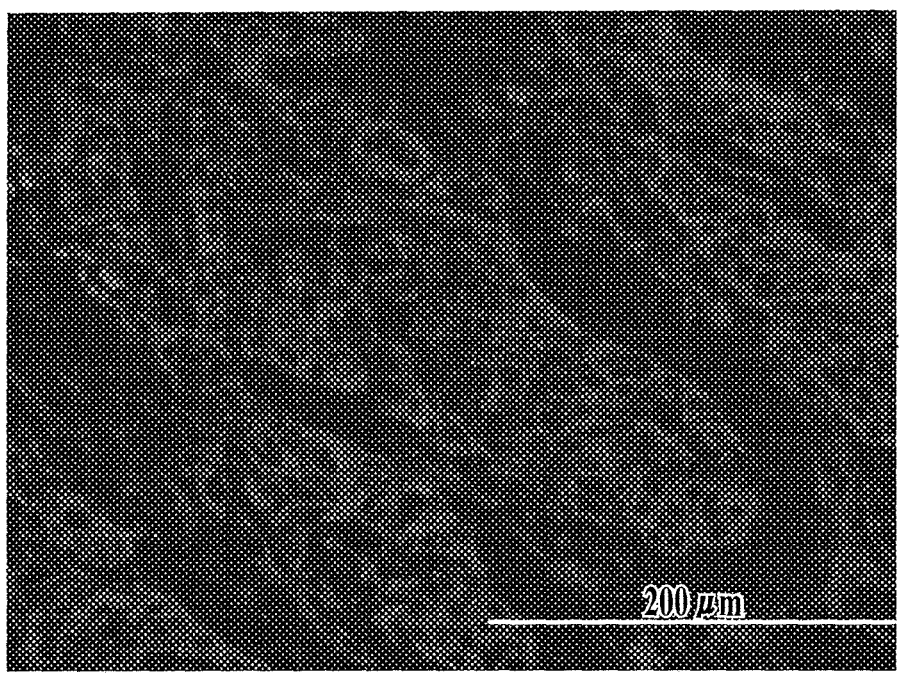
FIG. 4 is a diagram illustrating an exemplary fluorescent image.

The fluorescent image is a microscopic image obtained as follows: A tissue sample is stained with a staining reagent that contains nanoparticles (fluorescent particles) encapsulating a fluorescent substance and binding to a biological substance recognizing site specifically bindable and/or reactive to a specific biological substance. The tissue sample is irradiated with excitation light having a predetermined wavelength in the microscopic imaging device 1A to emit light (fluorescent light) from the fluorescent particles. The fluorescent image is enlarged, focused, and photographed. In other words, the fluorescent light appearing in the image represents the expression of the specific biological substance corresponding to the biological substance recognizing site in the tissue sample. FIG. 4 illustrates an exemplary fluorescent image.

<Acquisition of Fluorescent Image>

A method of acquiring a fluorescent image will now be described in detail. A staining reagent used in acquisition of a fluorescent image and a method of staining a tissue sample with a staining reagent will also be described.

[Fluorescent Substance]

Examples of fluorescent substances used in the staining reagent for acquiring a fluorescent image include organic fluorescent dyes and quantum dots (semiconductor particles). The fluorescent substances preferably emit visible light to near-infrared light having a wavelength in the range of 400 to 1100 nm when excited by ultraviolet light to near-infrared light having a wavelength in the range of 200 to 700 nm.

Examples of the organic fluorescent dyes include fluorescein dye molecules, rhodamine dye molecules, Alexa Fluor (made by Invitrogen Corporation) dye molecules, BODIPY (made by Invitrogen Corporation) dye molecules, cascading dye molecules, coumarin dye molecules, eosin dye molecules, NBD dye molecules, pyrene dye molecules, Texas Red dye molecules, and cyanine dye molecules.

Specific examples thereof include 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 6G, tetramethylrhodamine, X-rhodamine, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (made by Invitrogen Corporation), methoxycoumarin, eosin, NBD, pyrene, Cy5, Cy5.5, and Cy7. These organic fluorescent dyes may be used alone or in combination.

The quantum dot may contain Group II-VI compounds, Group III-V compounds, or Group IV elements as a component (also referred to as a "Group II-VI quantum dot", "Group III-V quantum dot", or "Group IV quantum dot", respectively) can be used. These quantum dots may be used alone or in combination.

Specific examples thereof include, but should not be limited to, CdSe, CdS, CdTe, ZnSe, ZnS, ZnTe, InP, InN, InAs, InGaP, GaP, GaAs, Si, and Ge.

[Fluorescent Substance-Encapsulating Nanoparticles]

The fluorescent substance-encapsulating nanoparticles (fluorescent particles) in the present embodiment refers to nanoparticles containing a dispersed fluorescent substance. The fluorescent substance and the nanoparticles may be chemically bonded or not. The nanoparticles may be composed of any material. Examples thereof include polystyrene, poly(lactic acid), silica, and melamine.

Quantum dots having cores of quantum dots and outer shells may be used as fluorescent particles. Throughout the specification, the quantum dot having a shell is represented, for example, as CdSe/ZnS where the core is CdSe and the shell is ZnS. Examples of usable quantum dots having cores of quantum dots and shells include, but should not be limited to, CdSe/ZnS, CdS/ZnS, InP/ZnS, InGaP/ZnS, Si/SiO$_2$, Si/ZnS, Ge/GeO$_2$, Ge/ZnS.

Quantum dots surface treated with an organic polymer may also be used when necessary. Examples of such quantum dots include CdSe/ZnS having surface carboxy groups (made by Invitrogen Corporation), and CdSe/ZnS having surface amino groups (made by Invitrogen Corporation).

The fluorescent particles used in the present embodiment can be prepared by any known method. Encapsulation of the fluorescent dye in the nanoparticles may be performed by any method of introducing a fluorescent dye into a resin, for example, bonding fluorescent dye molecules to raw-material monomers to synthesize particles or adsorbing a fluorescent dye to a resin.

Polystyrene nanoparticles encapsulating an organic fluorescent dye can be prepared by the copolymerization process described in U.S. Pat. No. 4,326,008 (1982) using an organic dye having a polymerizable functional group, or impregnation of polystyrene nanoparticles with an organic fluorescent dye, which is disclosed in U.S. Pat. No. 5,326,692 (1992).

Polymer nanoparticles encapsulating quantum dots can be prepared by impregnation of polystyrene nanoparticles with quantum dots, which is disclosed in Nature Biotechnology vol. 19, p. 631 (2001).

The fluorescent particles used in the present embodiment may have any average particle size. Fluorescent particles having a large particle size readily lead to saturation of the luminance and thus obstruction of accurate measurement of the luminance when they are close to each other. Fluorescent particles having a small particle size lead to small integrated luminance signals from the fluorescent particles buried in background noises (noises of the camera or autofluorescence of cells). Accordingly, the average particle size is preferably 40 to 280 nm.

The average particle size is determined as follows: Cross-sectional areas of particles are measured in an electron microscopic photograph taken with a scanning electron microscope (SEM). The observed area of each particle is regarded as the area of a circle, and the diameter of the circle is defined as the particle size. In this application, the sizes of 1000 particles are measured, and the arithmetic average is defined as the average particle size.

[Binding of Biological Substance Recognizing Site to Fluorescent Particle]

The biological substance recognizing site according to the present embodiment is a site specifically bindable and/or reactive to a target biological substance. The target biological substance may be any biological substance specifically bindable to the site. Typical examples of the target biological substance include proteins (peptides), nucleic acids (oligonucleotides, polynucleotides), and antibodies. Accordingly, examples of a substance specifically bindable to the target biological substance include antibodies that can recognize the proteins as antigens, other proteins specifically bindable to the proteins, and nucleus acids having base sequences allowing hybridization to the nucleus acids. Specific examples thereof include an anti-HER2 antibody specifically bindable to HER2 or a protein to be expressed on surfaces of cells; a Ki67 antibody specifically bindable to Ki67 protein as a cell proliferation marker to be expressed in cell nuclei; an anti-ER antibody specifically bindable to an estrogen receptor (ER) to be expressed in cell nuclei; and an anti-actin antibody specifically bindable to actin that forms a cell skeleton. Among these antibodies, the anti-HER2 antibody, the anti-ER antibody, or the anti-Ki67 antibody is preferred because fluorescent particles bound to the antibody can be used in selection of drugs for breast cancer.

Examples of the specific antigens include the followings. The antibodies for recognizing these antigens are commercially available from a variety of antibody manufacturers, and can also be produced based on knowledge generally shared. Examples of the specific antigens include M. actin, M.S. actin, S.M. actin, ACTH, Alk-1, α1-antichymotrypsin, α1-antitrypsin, AFP, bcl-2, bcl-6, β-catenin, BCA 225, CA19-9, CA125, calcitonin, calretinin, CD1a, CD3, CD4, CD5, CD8, CD10, CD15, CD20, CD21, CD23, CD30, CD31, CD34, CD43, CD45, CD45R, CD56, CD57, CD61, CD68, CD79a, "CD99, MIC2", CD138, chromogranin, c-KIT, c-MET, collagen type IV, Cox-2, cyclin D1, keratin, cytokeratin (high molecular weight), pan-keratin, pan-keratin, cytokeratin 5/6, cytokeratin 7, cytokeratin 8, cytokeratin 8/18, cytokeratin 14, cytokeratin 19, cytokeratin 20, CMV, E-cadherin, EGFR, ER, EMA, EBV, factor VIII-related antigen, fascin, FSH, galectin-3, gastrin, GFAP, glucagon, glycophorin A, granzyme B, hCG, hGH, *Helicobacter pylori*, HBc antigen, HBs antigen, hepatocyte specific antigen, HER2, HSV-I, HSV-II, HHV-8, IgA, IgG, IgM, IGF-1R, inhibin, insulin, kappa L chain, Ki67, lambda L chain, LH, lysozyme, macrophage, melan A, MLH-1, MSH-2, myeloperoxidase, myogenin, myoglobin, myosin, neurofilament, NSE, p27 (Kip1), p53, p53, P63, PAX 5, PLAP, *Pneumocystis carinii*, Podoplanin (D2-40), PGR, prolactin, PSA, prostatic acid phosphatase, renal cell carcinoma, S100, somatostatin, spectrin, synaptophysin, TAG-72, TdT, thyroglobulin, TSH, TTF-1, TRAcP, tryptase, bilin, vimentin, WT1, and Zap-70.

In the case where the target biological substance is a nucleus acid, the following specific nucleus acid genes whose relations with diseases are pointed out can be exemplified. Probes recognizing these specific nucleus acid genes are commercially available as BAC probes, and can also be produced based on knowledge generally shared. Specific examples of the specific nucleus acid genes are listed below. Examples of genes related to proliferation of cancer or response rates of molecular target drugs include HER2, TOP2A, HER3, EGFR, P53, and MET. Known examples of cancer related genes are as follows. Examples of tyrosine kinase related genes include ALK, FLT3, AXL, FLT4 (VEGFR3, DDR1, FMS(CSF1R), DDR2, EGFR(ERBB1), HER4(ERBB4), EML4-ALK, IGF1 R, EPHA1, INSR, EPHA2, IRR(INSRR), EPHA3, KIT, EPHA4, LTK, EPHA5, MER(MERTK), EPHA6, MET, EPHA7, MUSK, EPHA8, NPM1-ALK, EPHB1, PDGFRα(PDGFRA), EPHB2, PDGFRβ(PDGFRB)EPHB3, RET, EPHB4, RON (MST1R), FGFR1, ROS(ROS1), FGFR2, TIE2(TEK), FGFR3, TRKA(NTRK1), FGFR4, TRKB(NTRK2), FLT1 (VEGFR1), and TRKC(NTRK3). Examples of breast cancer related genes include ATM, BRCA1, BRCA2, BRCA3, CCND1, E-Cadherin, ERBB2, ETV6, FGFR1, HRAS, KRAS, NRAS, NTRK3, p53, and PTEN. Examples of genes related to carcinoid tumors include BCL2, BRD4, CCND1, CDKN1A, CDKN2A, CTNNB1, HES1, MAP2, MEN1, NF1, NOTCH1, NUT, RAF, SDHD, and VEGFA. Examples of colorectal cancer related genes include APC, MSH6, AXIN2, MYH, BMPR1A, p53, DCC, PMS2, KRAS2 (or Ki-ras), PTEN, MLH1, SMAD4, MSH2, STK11, and MSH6. Examples of lung cancer related genes include ALK, PTEN, CCND1, RASSF1A, CDKN2A, RB1, EGFR, RET, EML4, ROS1, KRAS2, TP53, and MYC. Examples of liver cancer related genes include Axin1, MALAT1, b-catenin, p16 INK4A, c-ERBB-2, p53, CTNNB1, RB1, Cyclin D1, SMAD2, EGFR, SMAD4, IGFR2, TCF1, and KRAS. Examples of kidney cancer related genes include Alpha, PRCC, ASPSCR1, PSF, CLTC, TFE3, p54nrb/NONO, and TFEB. Examples of thyroid cancer related genes include AKAP10, NTRK1, AKAP9, RET, BRAF, TFG, ELE1, TPM3, H4/D10S170, and TPR. Examples of ovarian cancer related genes include AKT2, MDM2, BCL2, MYC, BRCA1, NCOA4, CDKN2A, p53, ERBB2, PIK3CA, GATA4, RB, HRAS, RET, KRAS, and RNASET2.

Examples of prostate cancer related genes include AR, KLK3, BRCA2, MYC, CDKN1B, NKX3.1, EZH2, p53, GSTP1, and PTEN. Examples of bone tumor related genes include CDH11, COL12A1, CNBP, OMD, COL1A1, THRAP3, COL4A5, and USP6.

The biological substance recognizing site may be bound to fluorescent particles with any bond. Examples of the binding form include covalent bond, ionic bond, hydrogen bond, coordination bond, physical adsorption, and chemical adsorption. Bonds having strong forces, such as covalent bond, are preferred in view of stability of the bond.

An organic molecule may link between the biological substance recognizing site and the fluorescent particle. For example, a poly(ethylene glycol) chain, such as SM(PEG)12 made by Thermo Scientific Inc., may be used to inhibit non-specific adsorption of a biological substance.

The biological substance recognizing site can be bound to fluorescent substance-encapsulating silica nanoparticles according to the same procedure in both the fluorescent substance composed of an organic fluorescent dye and that composed of a quantum dot. For example, the biological substance recognizing site may be bound to fluorescent substance-encapsulating silica nanoparticles with a silane coupling agent, which is widely used in binding of inorganic substances to organic substances. The silane coupling agent has an alkoxysilyl group at one terminal of the molecule to yield a silanol group through hydrolysis, and has a functional group, such as a carboxyl, amino, epoxy, or aldehyde group, at the other terminal. The silane coupling agent is bound to an inorganic substance through an oxygen atom of the silanol group. Specific examples thereof include mercaptopropyltriethoxysilane, glycidoxypropyltriethoxysilane, aminopropyltriethoxysilane, and silane coupling agents having a poly(ethylene glycol) chain (such as PEG-silane no. SIM6492.7 made by Gelest, Inc.). Tho or more silane coupling agents may be used in combination.

The organic fluorescent dye-encapsulating nanoparticles may be reacted with a silane coupling agent according to a known procedure. For example, the organic fluorescent dye-encapsulating nanoparticles are dispersed in pure water, and aminopropyltriethoxysilane is added to be reacted with the particles at room temperature for 12 hours. After the reaction is completed, the product is centrifuged or filtered to yield organic fluorescent dye-encapsulating nanoparticles having surfaces modified with aminopropyl groups. The amino group can be reacted with a carboxyl group in an antibody to bind the antibody with the organic fluorescent dye-encapsulating nanoparticle through an amido bond. A condensing agent, such as EDC (1-ethyl-3-[3-dimethylaminopropyl]carbodiimide hydrochloride: available from Pierce (registered trademark)), may also be used when necessary.

A linker compound having a site that can directly bind to an organic fluorescent dye-encapsulating nanoparticle modified with an organic molecule and a site that can bind to a molecular target substance may be used when necessary. Specifically, in use of sulfo-SMCC (sulfosuccinimidyl 4[N-maleimidomethyl]-cyclohexane-1-carboxylate: available from Pierce) having both a site selectively reactive with an amino group and a site selectively reactive with a mercapto group, amino groups of organic fluorescent dye-encapsulating nanoparticles modified with aminopropyltriethoxysilane can be bound to mercapto groups in antibodies to organic fluorescent dye-encapsulating nanoparticles having antibodies.

When the biological substance recognizing site is bound to each fluorescent substance-encapsulating polystyrene nanoparticle, the same procedure can be used both in the case where the fluorescent substance is an organic fluorescent dye and in the case where the fluorescent substance is a quantum dot. In other words, impregnation of polystyrene nanoparticles having a functional group, such as an amino group, with an organic fluorescent dye or a quantum dot can yield fluorescent substance-encapsulating polystyrene nanoparticles having the functional group. Use of EDC or sulfo-SMCC in the subsequent step can yield fluorescent substance-encapsulating polystyrene nanoparticles having antibodies.

[Staining Process]

The method of staining a tissue sample will now be described. The present invention can also be applied to samples of cells fixed onto substrates and others, besides tissue samples.

Samples applicable to the staining process described below can be prepared by any known method.

1) Deparaffinizing Step

A tissue sample is immersed in xylene in a vessel to remove paraffin. Deparaffinization may be performed at any temperature, for example, at room temperature. A preferred immersion time is 3 minutes or more and 30 minutes or less. Xylene may be replaced with fresh one during the immersion when necessary.

The tissue sample is then immersed in ethanol in a vessel to remove xylene. The immersion may be performed at any temperature, for example, at room temperature. A preferred immersion time is 3 minutes or more and 30 minutes or less. Ethanol may be replaced with fresh one during the immersion when necessary.

The tissue sample is then immersed in water in a vessel to remove ethanol. The immersion may be performed at any temperature, for example, at room temperature. A preferred immersion time is 3 minutes or more and 30 minutes or less. Water may be replaced with fresh one during the immersion when necessary.

2) Retrieval

A target biological substance is retrieved by a known process. The retrieval may be performed under any condition, and may be performed with a solution for retrieval, such as a 0.01 M citric acid buffer solution (pH: 6.0), a 1 mM EDTA solution (pH: 8.0), 5% urea, or a 0.1 M trishydrochloric acid buffer solution. An autoclave, microwaves, a pressure pan, or a water bath may be used as a heater. The retrieval may be performed at any temperature, for example, at room temperature. The sample may be activated at a temperature of 50 to 130° C. for 5 to 30 minutes.

The activated sample is then immersed in phosphate buffered saline (PBS) in a vessel to wash the sample. The immersion may be performed at any temperature, for example, at room temperature. A preferred immersion time is 3 minutes or more and 30 minutes or less. PBS may be replaced with fresh one during the immersion when necessary.

3) Staining with Fluorescent Particles Bound to Biological Substance Recognizing Site A dispersion of fluorescent particles bound to a biological substance recognizing site in PBS is placed on a tissue sample to react with a target biological substance. The type of the biological substance recognizing site bindable to the fluorescent particles can be varied to stain a variety of biological substances. In use of several types of fluorescent particles bound to different biological substance recognizing sites, these types of fluorescent particles bound to different biological substance recognizing sites in PBS may be premixed, or may be sequentially placed on the tissue sample.

The staining may be performed at any temperature, for example, at room temperature. A preferred reaction time is 30 minutes or more and 24 hours or less.

Prior to the staining with fluorescent particles, a known blocking agent, such as BSA-containing PBS, is preferably added dropwise to the tissue sample.

The stained tissue sample is then immersed in PBS in a vessel to remove unreacted fluorescent particles. The unreacted fluorescent particles may be removed at any temperature, for example, at room temperature. A preferred immersion time is 3 minutes or more and 30 minutes or less. PBS may be replaced with fresh one during the immersion when necessary. The tissue sample is covered with a cover glass to seal the tissue sample. A commercially available sealant may be used when necessary.

In the case where staining with an HE staining reagent is performed, HE staining is followed by the sealing of the tissue sample with the cover glass.

[Acquisition of Fluorescent Image]

A wide-field microscopic image (fluorescent image) of the stained tissue sample is taken with a microscopic imaging device 1A. In the microscopic imaging device 1A, an excitation light source and an optical filter for detecting fluorescent light are selected according to the absorption maximum wavelength of the fluorescent substance contained in the staining reagent and the wavelength of the fluorescent light from the fluorescent substance.

<Operation of Pathological Diagnosis Support System 100 (Including Image Processing Method)>

The operation of the pathological diagnosis support system 100 to acquire and analyze the fluorescent image and the bright field image described above will now be described. Throughout the specification, the operation will be described in an exemplary case of observing a tissue sample stained with a staining reagent containing a fluorescent particle bound to a biological substance recognizing site that can recognize a specific protein (HER2 protein in breast cancer tissues in this specification; hereinafter, referred to as a specific protein), but should not be limited to this.

An operator stains a tissue sample with two staining reagents, i.e., an HE staining reagent and a staining reagent containing a fluorescent labelling material composed of a fluorescent particle bound to the biological substance recognizing site that can recognize the specific protein.

The operator then takes a bright field image and a fluorescent image of the tissue sample with the microscopic imaging device 1A according to the procedures (a1) to (a5):

(a1) The operator places the tissue sample stained with the HE staining reagent and the staining reagent containing the fluorescent particles on a microscopic slide, and sets the slide on the slide stage of the microscopic imaging device 1A;

(a2) The operator sets a bright field unit, and adjusts the magnification for photographing and the focus to contain the target region of the tissue sample within the field;

(a3) The operator photographs the tissue sample with the photographing unit to generate image data of the bright field image, and transmits the image data to the image processing device 2A;

(a4) The bright field unit is replaced with a fluorescence unit; and (a5) The operator photographs the tissue sample with the photographing unit without changing the field and the magnification for photographing to generate image data of the fluorescent image, and transmits the image data to the image processing device 2A.

The image processing device 2A analyzes the bright field image and the fluorescent image.

Figure 5:
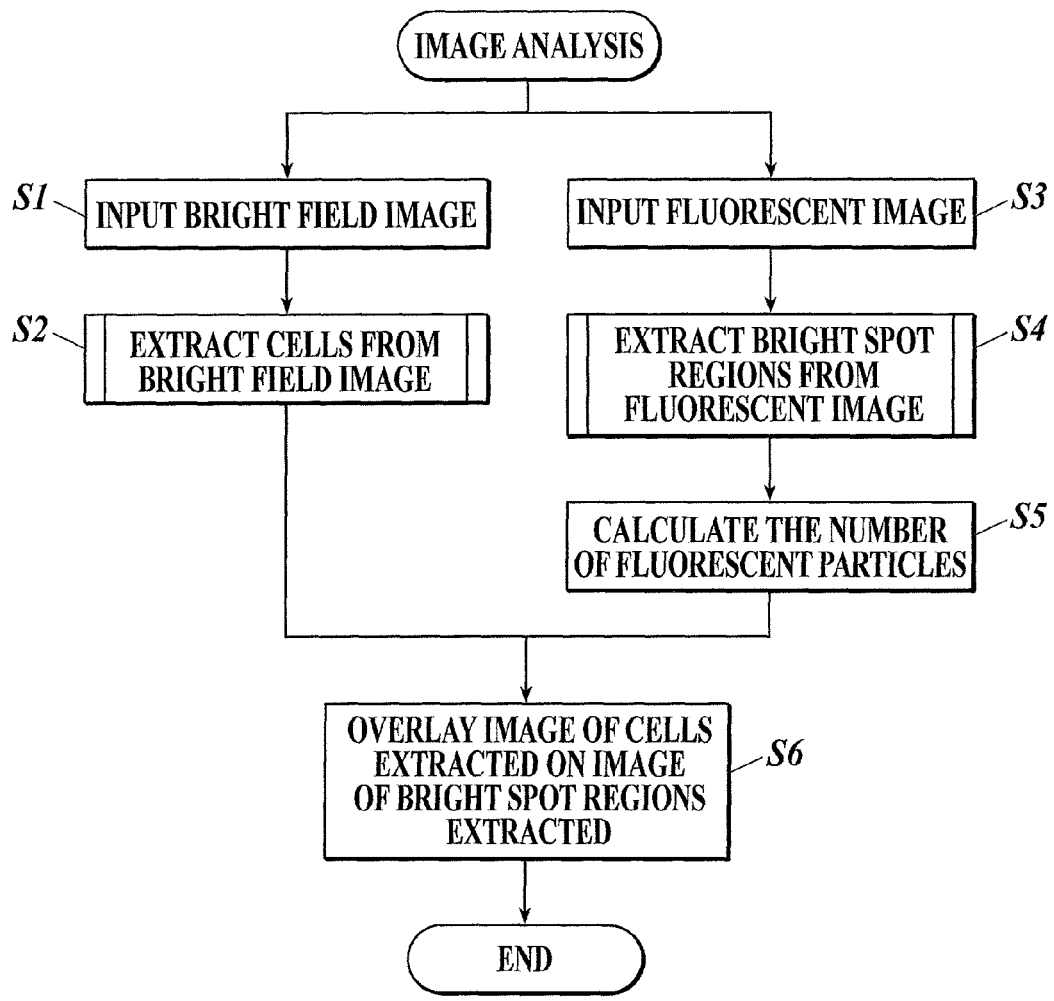
FIG. 5 is a flowchart illustrating image analysis processing executed by the control unit in FIG. 2.

FIG. 5 illustrates a flowchart of the image analysis in the image processing device 2A. The image analysis illustrated in FIG. 5 is executed in cooperation with the control unit 21 and the program stored in the storage unit 25.

If the bright field image transmitted from the microscopic imaging device 1A is input into the communication interface 24 (Step S1), cell regions are extracted from the bright field image (Step S2).

FIG. 6 illustrates the detailed flow of the process in Step S2. The process in Step S2 is executed in cooperation with the control unit 21 and the program stored in the storage unit 25.

Figure 7A:
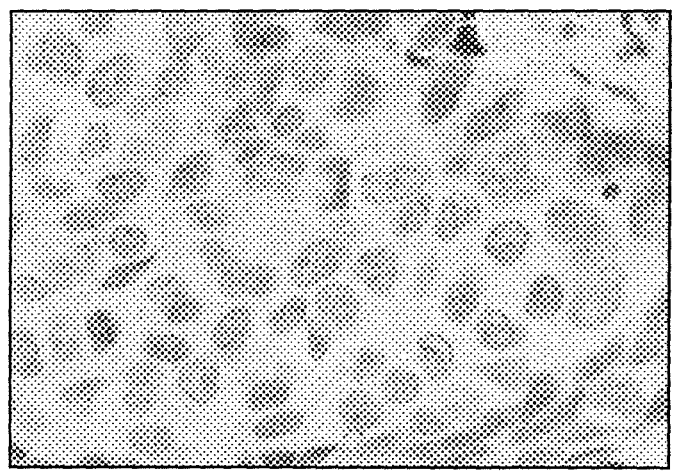
FIG. 7A is a diagram illustrating an exemplary bright field image.

In Step S2, the bright field image is converted into a monochromatic image (Step S201). FIG. 7A illustrates an exemplary bright field image.

The monochromatic image is then subjected to thresholding using a predetermined threshold to binarize the values of pixels (Step S202).

Figure 7B:
FIG. 7B is a diagram illustrating an image of cells extracted from the bright field image of FIG. 7A.

In the next step, noise reduction is executed (Step S203). The noise reduction can be executed, specifically, by subjecting the binary image to a closing process. In the closing process, dilation is executed a predetermined number of times, and then erosion is executed the same number of times. In the dilation, a target pixel is replaced with a white pixel if at least one white pixel is contained within the range from the target pixel to n×n pixels (where n is an integer of 2 or more). In the erosion, the target pixel is replaced with a black pixel if at least one black pixel is contained within the range from the target pixel to n×n pixels. The closing process can remove small regions, such as noises. FIG. 7B illustrates an exemplary image subjected to the noise reduction. The noise reduction generates an image (cell image, illustrated in FIG. 7B) of cells extracted from the bright field image.

In the next step, the image after the noise reduction is subjected to labelling to label each of the extracted cells (Step S204). In the labelling, the same label (number) is assigned to connected pixels to identify objects in an image. The labelling can identify the cells in the image after the noise reduction to label these cells.

Meanwhile, if the fluorescent image transmitted from the microscopic imaging device 1A is input into the communication interface 24 (Step S3), bright spot regions are extracted from the fluorescent image to calculate the integrated luminance of each bright spot region (Step S4: first calculating step).

Figure 8:
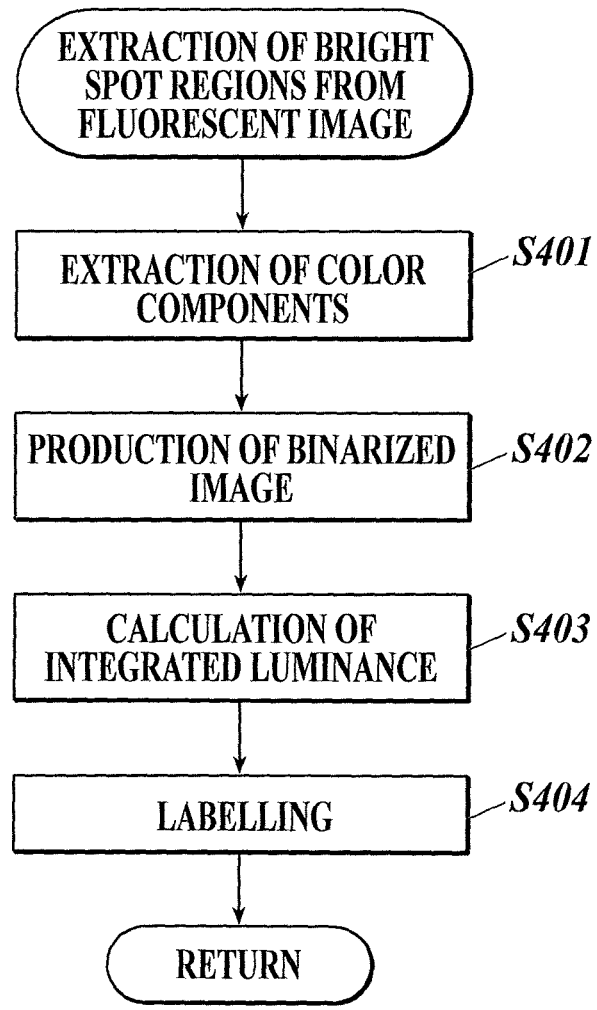
FIG. 8 is a flowchart illustrating the detailed processes of Step S4 in FIG. 5.

FIG. 8 illustrates the detailed flow of the process in Step S4. The process in Step S4 is executed in cooperation with the control unit 21 and the program stored in the storage unit 25.

In Step S4, color components are extracted from the fluorescent image according to the wavelengths of the fluorescent bright spots (Step S401).

Figure 9A:
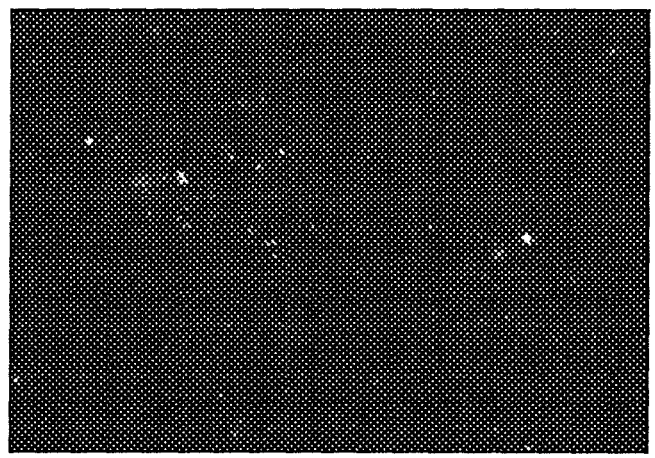
FIG. 9A is a diagram illustrating a fluorescent image.

FIG. 9A illustrates an exemplary fluorescent image.

In Step S401, for example, if the fluorescent particles emit light at a wavelength of 615 nm, only fluorescent bright spots having its corresponding wavelength component are extracted into an image.

In the next step, the extracted image is subjected to thresholding to generate a binary image (Step S402).

Noise removal to remove autofluorescent noise of cells and other unnecessary signal components may be executed prior to the thresholding. A low-pass filter, such as a Gaussian filter, or a high-pass filter, such as second derivative, is preferably used.

Figure 9B:
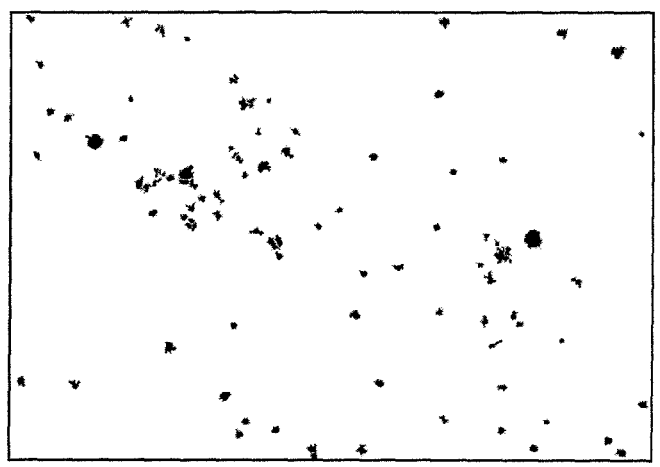
FIG. 9B is a diagram illustrating an image of bright spot regions extracted from the fluorescent image of FIG. 9A.
Figure 9C:
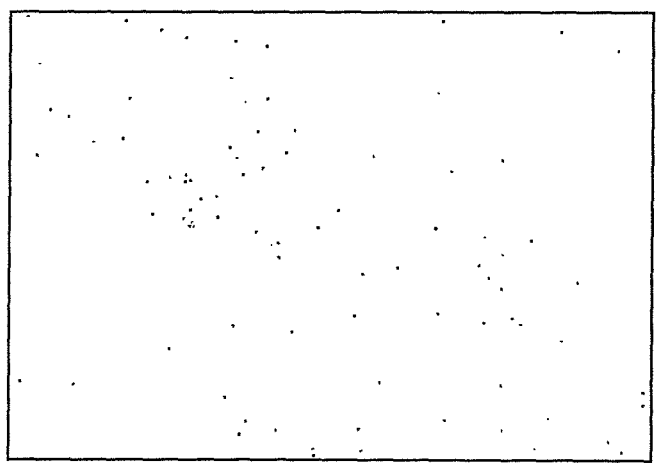
FIG. 9C is a diagram illustrating fluorescent bright spots.
Figure 10A:
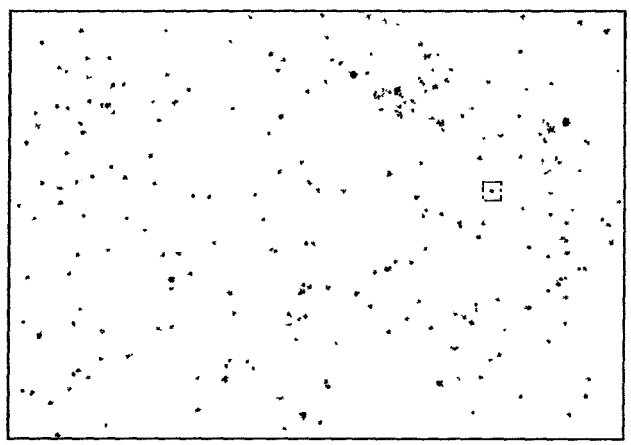
FIG. 10A is a diagram illustrating an image of extracted bright spot regions.
Figure 10B:
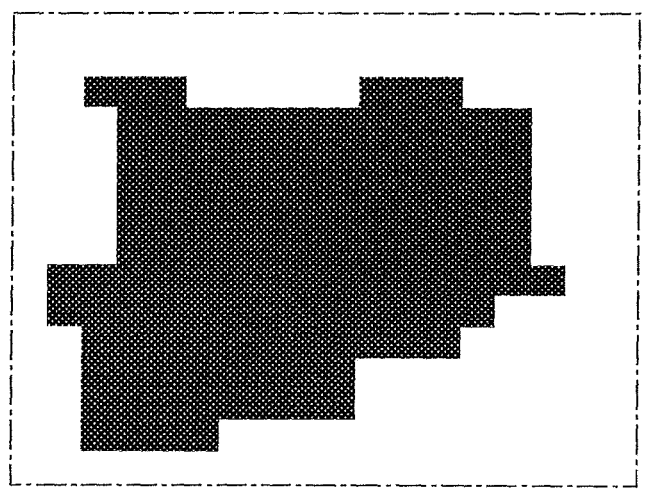
FIG. 10B is an enlarged diagram of one bright spot region extracted from FIG. 10A.
Figure 10C:
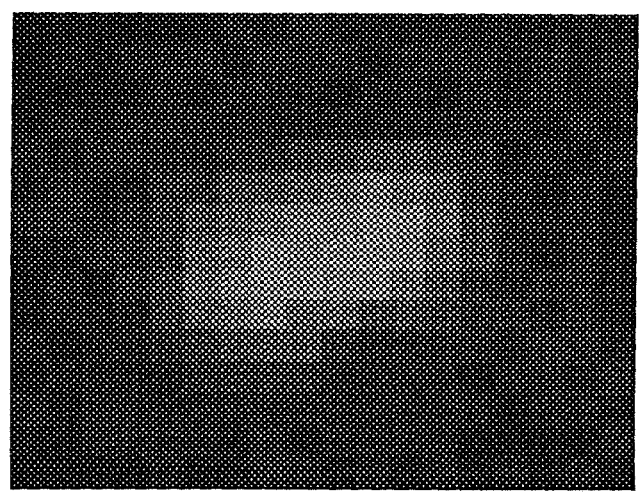
FIG. 10C is a diagram illustrating a fluorescent image corresponding to the bright spot region of FIG. 10B.
Figures 10D, 10E:
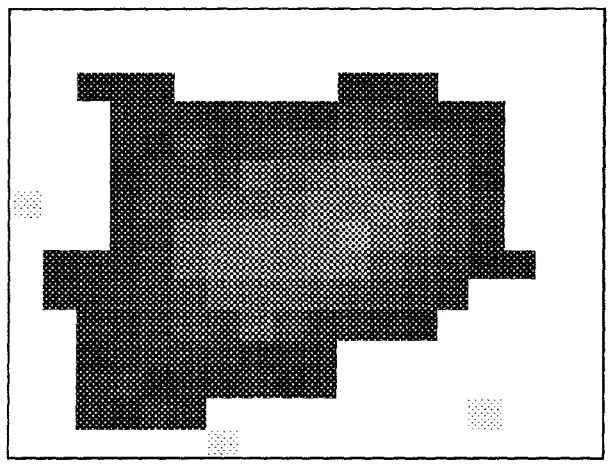
FIG. 10D is a diagram illustrating a second fluorescent image.
FIG. 10E is a table showing the luminance distribution in positions expressed by the X coordinate and the Y coordinate produced from the fluorescent image of FIG. 10D.

FIG. 9B illustrates an exemplary image of the bright spot regions extracted from the fluorescent image. In this image, these extracted bright spot regions have centers composed of fluorescent bright spots illustrated in FIG. 9C.

In the next step, an integrated luminance is calculated in each of the bright spot regions extracted from the fluorescent image (Step S403). In Step S403, as illustrated in FIGS. 10A to 10E, after an image of the bright spot regions (FIG. 10A) extracted from the fluorescent image is generated, an image of each extracted bright spot region (FIG. 10B) is overlaid on a portion of the fluorescent image (FIG. 10C) corresponding to the bright spot region. The image of the extracted bright spot region is masked to generate a second fluorescent image (FIG. 10D) from the fluorescent image corresponding to the bright spot region. The luminance distribution in positions expressed by the X coordinate and the Y coordinate (FIG. 10E) is produced from the second fluorescent image. The integrated luminance of the bright spot region is obtained by integration of the values shown in the luminance distribution.

In the next step, the second fluorescent image is subjected to labelling to label each of the extracted bright spot regions (Step S404).

After the process in Step S4 is completed, the step returns to the process in FIG. 5 to calculate the number of fluorescent particles contained in each bright spot region in Step S5 (second calculating step) using the average luminance per fluorescent particle preliminarily calculated and stored in the storage unit 25.

Figure 11A:
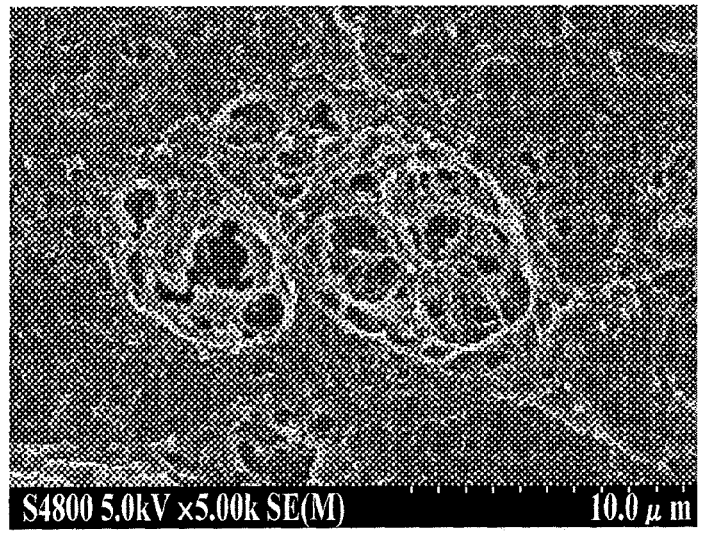
FIG. 11A is a diagram illustrating an exemplary SEM image of fluorescent particles.
Figure 11B:
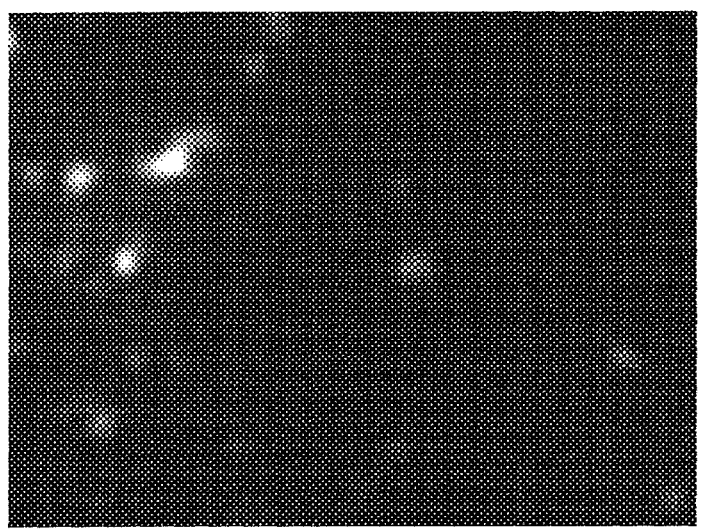
FIG. 11B is a diagram illustrating a fluorescent image of the same region as that of the SEM image in FIG. 11A.
Figure 11C:
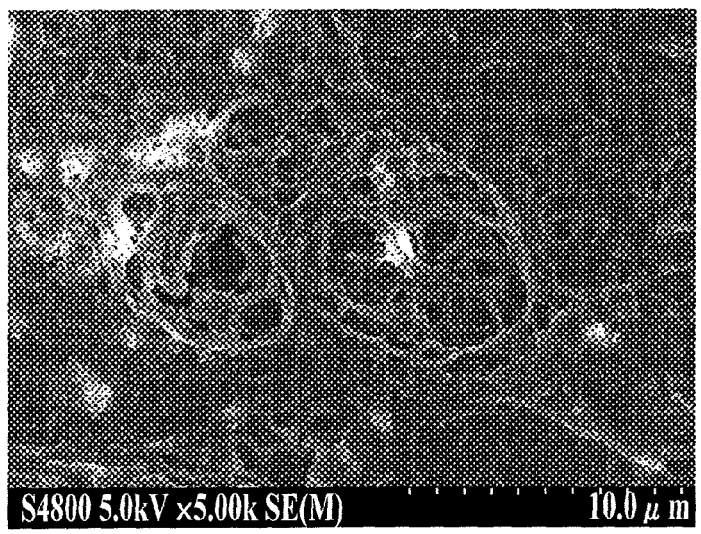
FIG. 11C is a diagram illustrating an overlaid image of the SEM image of FIG. 11A and the fluorescent image of FIG. 11B.

The average luminance per fluorescent particle is calculated as follows: An SEM image (FIG. 11(*a*)) is taken from a tissue sample stained with fluorescent particles or from a microscopic slide glass having dispersed fluorescent particles. In the next step, a fluorescent image (FIG. 11(*b*)) having a region substantially identical to that taken in the SEM image is taken as in Steps S3 and S4 to determine the integrated luminance of fluorescent bright spots. The SEM image and the fluorescent image are overlaid as illustrated in FIG. 11(*c*) to actually count the number of fluorescent particles present in each bright spot region.

The average luminance per fluorescent particle is calculated from the relationship between the integrated luminance actually determined from the fluorescent image and the number of fluorescent particles actually counted from the SEM image. For example, the integrated luminance of each bright spot region is divided by the number of fluorescent particles in the bright spot region to calculate the average integrated value per fluorescent particle. Alternatively, a scatter plot may be created where the number of particles in the bright spot region as the abscissa is plotted against the integrated luminance as the ordinate, and the average luminance may be calculated from the slope of the line of best fit.

The integrated luminance of each bright spot region determined from the fluorescent image of the tissue sample is divided by the average luminance per fluorescent particle to calculate the number of fluorescent particles in each bright spot region (Step S5). The information of the calculated number of fluorescent particles in each bright spot region is added to the information of the label of the bright spot region assigned in Step S404.

After the processes in Step S2 and Step S5 are completed, an overlaying process (Step S6) is performed on the cell image (FIG. 7B) and the bright spot region image (FIG. 9B) to display the distribution of the bright spot regions on cells on the display unit 23 of the image processing device 2A, and the number of fluorescent particles per cell is calculated.

According to the present embodiment, cells are extracted through the processes in Steps S1 and S2. The number of fluorescent particles in each bright spot region is calculated through Steps S3 to S5. Through the process of Step S6, the distribution of the bright spot regions on the cells is displayed in a specific form to calculate the number of fluorescent particles per cell. Such an average luminance per fluorescent particle preliminarily determined enables calculation of the number of fluorescent particles in each bright spot region, and thus accurate quantitative determination of the number of specific biological substances expressed in the tissue sample.

The description of the embodiment is a suitable example of the present invention, and the present invention should not be limited to this.

The average luminance per fluorescent particle is not limited to a default value stored in the storage unit 25. A user of the pathological diagnosis support system 100 may calibrate the average luminance per fluorescent particle. For example, the user may take a fluorescent image and an SEM image from a slide glass having dispersed fluorescent particles, calculate the average luminance per fluorescent particle according to the procedure described above, and store the average luminance in the storage unit 25. This operation enables calculation of the number of fluorescent particles contained in each bright spot region using the average luminance determined by the user.

Alternatively, after the target tissue sample is photographed, a fluorescent image may be taken from a sample of fluorescent particles under the same photographing conditions as those in photographing of the tissue sample, and be checked against an SEM image to calculate the average luminance per fluorescent particle. The average luminance is stored in the storage unit 25, and the steps in Step S5 and S6 are re-executed to recalculate the number of fluorescent particles contained in each bright spot region.

Since the average luminance can be calibrated, accurate results in count can be obtained, for example, in the cases where the intensity of fluorescent light emitted from fluorescent particles changed after long-term storage or a user adjusts the intensity of excitation light while taking a fluorescent image from a tissue sample.

In calculation of the average luminance per fluorescent particle, the number of fluorescent particles may be actually counted from an image taken with a confocal microscope, besides a bright field image taken with an SEM.

In the present embodiment, the integrated luminance of each bright spot region calculated in Step S4 is divided by the average luminance per fluorescent particle in Step S5 to calculate the number of fluorescent particles contained in each bright spot region. Alternatively, the integrated luminances of bright spot regions contained in a single cell may be added from the distribution of bright spot regions on cells displayed in Step S6, and may be divided by the average luminance per fluorescent particle to calculate the total number of fluorescent particles on the cell.

While only one specific protein is targeted in the embodiment, two or more types of fluorescent particles emitting light at different wavelengths may be used for a plurality of specific proteins.

In such a case, color components are extracted through filters in Step S401. The processes in Steps S402 to S5 are executed for each of the extracted color components (wavelength components). In Step S6, a cell image and fluorescent particle images generated for the respective color components are overlaid.

The description above discloses an example in which an HDD or a semiconductor nonvolatile memory is used as a computer-readable medium for the program according to the present invention, but the present invention should not be limited to this. Another computer-readable medium may also be used, for example, a portable recording medium, such as CD-ROM. Carrier waves can also be used as a medium that provides data of the program according to the present invention through a communication line.

The detailed configurations and operations of the devices forming the pathological diagnosis support system 100 can also be appropriately modified within the scope of the gist of the present invention.

(A) Preparation of Staining Reagent (a)

(A-1) Preparation of Fluorescent Substance-Encapsulating Melamine Nanoparticles

A red fluorescent dye Sulforhodamine 101 (made by Sigma-Aldrich Corporation) (14.4 mg) as a fluorescent substance was dissolved in water (22 mL). A 5% aqueous solution (2 mL) of an emulsifier for emulsion polymerization EMALGEN (registered trademark) 430 (polyoxyethylene oleyl ether, made by Kao Corporation) was added to the solution. The solution was heated to 70° C. with stirring on a hot stirrer, and 0.65 g of a melamine resin raw material NIKALAC MX-035 (made by NIPPON CARBIDE INDUSTRIES CO., INC.) was added to the solution.

A 10% aqueous solution (1000 µL) of dodecylbenzenesulfonic acid (made by KANTO CHEMICAL CO., INC.) as a surfactant was added to the solution, and was stirred at 70° C. for 50 minutes. The solution was heated to 90° C., and was stirred for 20 minutes at the temperature. The fluorescent substance-encapsulating melamine nanoparticles were washed with pure water to remove impurities, such as excess resin raw material and excess fluorescent dye.

Specifically, the dispersion was centrifuged with a centrifuge (Micro Cooling Centrifuge 3740 made by Kubota Corporation) at 20000 G for 15 minutes to remove the supernatant. Ultrapure water was added, and the solution was redispersed by ultrasonic waves. This washing operation on the fluorescent substance-encapsulating melamine nanoparticles through centrifugation, removal of the supernatant, and redispersion in ultrapure water was repeated five times.

The fluorescent substance-encapsulating melamine nanoparticles were observed with a scanning electron microscope (SEM; S-800 made by Hitachi, Ltd.). The average particle size was 158 nm.

Fluorescent substance-encapsulating melamine nanoparticles having an average particle size of 40 nm was prepared as in the process of preparing fluorescent substance-encapsulating melamine nanoparticles except that the amount of Sulforhodamine 101 (made by Sigma-Aldrich Corporation) was 5.25 mg and the amount of the melamine resin raw material NIKALAC MX-035 (made by NIPPON CARBIDE INDUSTRIES CO., INC.) was 0.21 g.

Fluorescent substance-encapsulating melamine nanoparticles having an average particle size of 80 nm were prepared as in the process of preparing the fluorescent substance-encapsulating melamine nanoparticles except that the amount of Sulforhodamine 101 (made by Sigma-Aldrich Corporation) was 10.5 mg and the amount of the melamine resin raw material NIKALAC MX-035 (made by NIPPON CARBIDE INDUSTRIES CO., INC.) was 0.43 g.

Fluorescent substance-encapsulating melamine nanoparticles having an average particle size of 280 nm were prepared as in the process of preparing the fluorescent substance-encapsulating melamine nanoparticles except that the amount of Sulforhodamine 101 (made by Sigma-Aldrich Corporation) was 20.3 mg and the amount of the melamine resin raw material NIKALAC MX-035 (made by NIPPON CARBIDE INDUSTRIES CO., INC.) was 0.81 g.

Fluorescent substance-encapsulating melamine nanoparticles having an average particle size of 320 nm were prepared as in the process of preparing fluorescent substance-encapsulating melamine nanoparticles except that the amount of Sulforhodamine 101 (made by Sigma-Aldrich Corporation) was 21.4 mg and the amount of the melamine resin raw material NIKALAC MX-035 (made by NIPPON CARBIDE INDUSTRIES CO., INC.) was 0.86 g.

The fluorescent substance-encapsulating melamine nanoparticles were positively charged because the melamine resin had a large amount of amino groups in the skeleton. The charges of the resin particles were evaluated by resin component analysis by NMR or IR and measurement of the zeta potential.

The fluorescent substance-encapsulating melamine nanoparticles (0.1 mg) were dispersed in ethanol (1.5 mL), and aminopropyltrimethoxysilane (LS-3150, made by Shin-Etsu Chemical Co., Ltd.) (2 µL) was added to perform a reaction for eight hours. Hydroxyl groups present on the resin surfaces of the fluorescent substance-encapsulating melamine nanoparticles was thereby converted to amino groups by surface amination.

(A-2) Preparation of Fluorescent Substance-Encapsulating Silica Nanoparticles

A red fluorescent Texas Red dye (3.4 g) as a fluorescent substance and 3-aminopropyltrimethoxysilane (KBM903, available from the Shin-Etsu Silicone) (3 µL) were mixed in DMF to yield an organoalkoxysilane compound. The organoalkoxysilane compound (0.6 mL) was mixed with 48 mL of ethanol, 0.6 mL of tetraethoxysilane (TEOS), 2 mL of water, and 1.3 mL of 28% aqueous ammonia for three hours. The mixed solution prepared in the above step was centrifuged at 10000 G for 20 minutes to remove the supernatant. Ethanol was added to disperse the precipitate. The dispersion was centrifuged again. Washing with ethanol and that with pure water as above were each repeated twice to prepare fluorescent substance-encapsulating silica nanoparticles.

The fluorescent substance-encapsulating silica nanoparticles were observed with an SEM. The average particle size was 50 nm.

Fluorescent substance-encapsulating silica nanoparticles having an average particle size of 280 nm were prepared as in the process of preparing fluorescent substance-encapsulating silica nanoparticles except that the amount of 28% aqueous ammonia was 2.5 mL.

(A-3) Binding of Anti-HER2 Antibody to Fluorescent Particles

The concentrations of the fluorescent particles prepared in (A-1) and (A-2) were each adjusted to 3 nM with PBS containing 2 mM of EDTA. SM(PEG)12 (made by Thermo Scientific, Inc.) was added to each solution such that the final concentration was 10 mM. The mixed solution was reacted at 20° C. for one hour. The mixed solution was centrifuged at 10000 G for 20 minutes to remove the supernatant. PBS containing 2 mM of EDTA was added to disperse the precipitate, and the dispersion was centrifuged again. The washing operation was performed three times as above to prepare fluorescent particles having terminal maleimido groups.

Thiol groups were added to streptavidin (made by Wako Pure Chemical Industries, Ltd.) with SATA, and the product was filtered through a gel filtration column to prepare a solution of streptavidin bindable to the maleimido groups of the fluorescent particles.

The fluorescent particles having terminal maleimido groups and the streptavidin were mixed in PBS containing 2 mM of EDTA to be reacted at room temperature for one hour. Mercaptoethanol (10 mM) was added to terminate the reaction. The resulting solution was condensed with a centrifugal filter having an opening of 0.65 µm, and was passed through a gel filtration column to remove unreacted streptavidin and other impurities. Final fluorescent particles binding to streptavidin were thereby yielded.

Anti-HER2 antibodies were bound to the fluorescent particles by the following steps (1) to (12):

Step (1): 1 mg of fluorescent particles was dispersed in pure water (5 mL); An aqueous solution (100 µL) of aminopropyltriethoxysilane (LS-3150, made by Shin-Etsu Chemical Co., Ltd.) was added, and was stirred at room temperature for 12 hours.

Step (2): The reaction mixture was centrifuged at 10000 G for 60 minutes to remove the supernatant.

Step (3): Ethanol was added to disperse the precipitate, and the solution was centrifuged again. Washing with ethanol and that with pure water were each performed once as above.

The nanoparticles were measured by Fourier transform infrared (FT-IR) spectroscopy. Modification of the nanoparticles with amino groups was confirmed from observation of absorption derived from amino groups.

Step (4): The concentration of the amino group-modified nanoparticles prepared in Step (3) was adjusted to 3 nM with PBS containing 2 mM of ethylenediaminetetraacetic acid (EDTA).

Step (5): The solution prepared in Step (4) was mixed with SM(PEG)12 (made by Thermo Scientific, Inc., succinimidyl-[(N-maleomidopropionamid)-dodecaethyleneglycol] ester) such that the final concentration was 10 mM, and the reaction was performed for one hour.

Step (6): The mixed reaction solution was centrifuged at 10000 G for 60 minutes to remove the supernatant.

Step (7): PBS containing 2 mM of EDTA was added to disperse the precipitate, and the dispersion was centrifuged again. This washing procedure was repeated three times. Finally, the product was redispersed in 500 µL of PBS to yield fluorescent particles for binding to antibodies.

Step (8): To a solution of the anti-HER2 antibody (100 µg) in PBS (100 µg), 1 M dithiothreitol (DTT) was added and reacted for 30 minutes.

Step (9): The reaction mixture was passed through a gel filtration column to remove excess DTT. A solution of reduced anti-HER2 antibodies bindable to the fluorescent particles was thereby prepared.

Step (10): The solution of dispersed fluorescent particles for binding to antibodies, which were prepared from fluorescent particles as a starting raw material in Step (7), and the reduced anti-HER2 antibody solution prepared in Step (9) were mixed in PBS to perform a reaction for one hour.

Step (11): 10 mM mercaptoethanol (4 µL) was added to terminate the reaction.

Step (12): The reaction mixture was centrifuged at 10000 G for 60 minutes to remove the supernatant. PBS containing 2 mM of EDTA was added to disperse the precipitate. The solution was centrifuged again. This washing operation was performed as above three times. Finally, the product was redispersed in 500 µL of PBS to yield fluorescent particles (Staining reagent (a)) bound to anti-HER2 antibodies.

(B) Preparation of Staining Reagent (b) (Derived from Quantum Dot)

Anti-HER2 antibodies were bound to quantum dots having an average particle size of 18 nm according of the protocol of Qdot Antibody Conjugation Kit made by Life Technologies Corporation. The procedure will be described in detail below.

Anti-HER2 antibodies were reduced with 20 mM dithiothreitol (DTT), and the product was passed through a gel filtration column to remove excess DTT. A reduced antibody solution was thereby prepared. Quantum dots were reacted with SMCC, and the reaction product was passed through a gel filtration column to remove excess SMCC. Maleimidized quantum dots reactive with the reduced antibodies were thereby prepared. The reduced antibodies and the maleimidized quantum dots were mixed, and were reacted for one hour. Mercaptoethanol was added to adjust the concentration to 100 µM to terminate the reaction. The solution after the termination of the reaction was gel filtered to yield anti-HER2 antibodies (Staining reagent (b)) bound to the quantum dots.

(C) Staining of Tissues

Tissue samples were immunostained with Staining reagents (a) and (b) according to Steps (1) to (11) below. The details of the tissue samples will be described later.

Step (1): Tissue samples were immersed in xylene in a vessel for 30 minutes. Xylene was replaced three times during immersion.

Step (2): The tissue samples were immersed in ethanol in a vessel for 30 minutes. Ethanol was replaced three times during immersion.

Step (3): The tissue samples were immersed in water in a vessel for 30 minutes. Water was replaced three times during immersion.

Step (4): The tissue samples were immersed in a 10 mM citric acid buffer solution (pH: 6.0) for 30 minutes.

Step (5): The tissue samples were autoclaved at 121° C. for 10 minutes.

Step (6): The autoclaved tissue samples were immersed in PBS in a vessel for 30 minutes.

Step (7): PBS containing 1% BSA was placed on the tissue samples, and the tissue samples were left for one hour.

Step (8): Staining reagents (a) and (b) diluted to 0.05 nM with PBS containing 1% BSA were separately placed on the tissue samples, and the tissue samples were left for three hours.

Step (9): The tissue samples stained with Staining reagent (a) and the tissue samples stained with Staining reagent (b) were immersed in PBS in different vessels for 30 minutes.

Step (10): The tissue samples were fixed with 4% neutral paraformaldehyde solution for 10 minutes.

Step (11): Aquatex made by Merck Chemicals GmbH was added dropwise, and cover glasses were placed on the tissue samples to seal the tissue samples.

(D) Calculation of Average Luminance Per Particle

Staining reagents (a) and (b) (concentration of particles: 0.2 nM) were dispersed on slide glasses, and a fluorescent image was taken from each of the slide glasses according to Steps S3 and S4 to determine the integrated luminances of 100 fluorescent bright spots. In the next step, an SEM image was taken from a region substantially identical to that taken in each fluorescent image, and was overlaid on the fluorescent image to count the number of particles present in each bright spot region. The integrated luminances of 100 bright spot regions were divided by the number of particles actually counted from the SEM image to determine the average luminance per particle.

(E) Image Analysis

Microscopic images (bright field image and fluorescent image) were taken with a laser confocal microscope FV1000-D made by Olympus Corporation. The fluorescent image was taken at a central wavelength of 615 nm under excitation light having an excitation wavelength of 605 nm. The microscope and photographing conditions during acquisition of the fluorescent image are identical to those during acquisition of the fluorescent image for calculation of the average luminance per fluorescent particle in (D).

In eight spots on the slide glass, the number of fluorescent bright spots contained in the entire field or 30 cells was counted to calculate the average luminance. The process of counting the number of bright spots will be described below.

(E-1) Count of the Number of Bright Spots by Process of the Present Invention

In Example, the fluorescent image was subjected to image analysis in FIG. 5 to calculate the number of bright spots.

(E-2) Count of the Number of Bright Spots by Conventional Process

In Comparative Example, the number of bright spots was counted by the process disclosed in Japanese Patent Application Laid-Open No. 2013-057631. Specifically, a binarized image was produced from a fluorescent image based on a predetermined higher threshold and lower threshold. These thresholds may be determined by statistical threshold determination, such as binarization according to Otsu's discrimination analysis (Nobuyuki Otsu; Hanbetsu oyobi Saishojijokijunni motoduku Jidosikiichi senteiho (Method of Automatically Selecting Thresholds Based on Discrimination and Least Square Criterion), Journal of The Institute of Electronics, Information and Communication Engineers, Vol. J63-D, No. 4, pp. 349-356, 1980), for example. The number of bright spots in the binarized image was counted with bright spot measuring software "G-count" made by G-Angstrom K.K.

In count of the number of bright spots per cell, the bright field image taken in Step S2 of FIG. 5 and the fluorescent image taken in Step S3 of FIG. 5 were overlaid to calculate the number of bright spots in each cell region.

<Experimental Result 1>

In samples of Staining reagents (a) and (b) (concentration of particles: 0.2 nM) dropped on slide glasses, the number of bright spots per field was counted by the process (E-1) of the present invention and the conventional process (E-2). The number of fluorescent particles in the same field was counted with an SEM, and was determined as the true number of fluorescent particles.

The discrepancy between the number of bright spots counted by the process (E-1) of the present invention or by the conventional process (E-2) in the fluorescent image and the true number of particles counted with the SEM (true number) was calculated from the following expression. The results are shown in Table 1.

Discrepancy (%)=(1−(the number of bright spots)/(the true number of particles))×100

TABLE 1

| | | Diameter of fluorescent particle[nm], Material | | | | | |
|---|---|---|---|---|---|---|---|
| | | 18 Quantum dot | 40 Melamine | 50 Silica | 80 Melamine | 158 Melamine | 280 Silica |
| Discrepancy from true value [%] | Example 1 | 7 | 3 | 3 | 2 | 7 | 7 |
| | Comparative Example 1 | 11 | 30 | 30 | 43 | 25 | 30 |

Table 1 shows that the discrepancy between the number of bright spots determined from the fluorescent image and the true number of particles was 11 to 43% in the count by the conventional process (Comparative Example 1), and was 2 to 7% in the count by the process of the present invention (Example 1), indicating a significant enhancement in accuracy of count of the number of bright spots.

Since the process of the present invention can accurately calculate the number of adjacent fluorescent particles contained in one bright spot region, the number of fluorescent particles approximate to the true number of particles was obtained.

In the count of the number of bright spots according to the process (E-1) of the present invention and the conventional process (E-2), although a plurality of fluorescent particles was calculated as one bright spot rather than individual fluorescent particles in some cases, the number of fluorescent particles calculated as bright spots was not greater than the true number. Accordingly, it can be determined that a larger calculated number of bright spots are closer to the true number.

<Experimental Result 2>

Human breast tissue samples (tissue array slide (CB-A712) made by Cosmo Bio Co., Ltd.) were immunostained with Staining reagents (a) and (b). The number of bright spots per field was counted by the process (E-1) of the present invention and the conventional process (E-2). The results are shown in Table 2.

reason, the number of bright spots and the measurement accuracy were reduced also in calculation by the process of the present invention.

Tissue samples stained with Staining reagent (a) derived from melamine having an average particle size of 320 nm had a larger luminance per particle, and often their bright spot regions in fluorescent images had saturated luminances. For this reason, the number of bright spots and the measurement accuracy were reduced also in calculation by the process of the present invention.

Such a reduction in measurement accuracy due to the difference in the particle size (luminance) of the fluorescent particle can be improved through adjustment of the photographic conditions for fluorescent images and calibration of the fluorescent images.

The number of bright spots per field was also counted by the process (E-1) of the present invention and the conventional process (E-2) using Staining reagent (a') containing fluorescent particles bound to anti-Ki67 antibodies by the same procedure as in (A-3). The results were similar to those in Example 2 using Staining reagent (a).

<Experimental Result 3>

Seven cultured cells containing the HER2 protein expressed at different expression levels (Cord No.: HS5 (CRL11882), SW480, Hela, COLO201, ZR-75-1 (CRL1500), SK-BR-3, and SK-OV-3 in ascending order of expression level) were immunostained with Staining reagents (a) and (b). The levels of the HER2 protein

TABLE 2

| | | Diameter of fluorescent particle[nm], Material | | | | | | |
|---|---|---|---|---|---|---|---|---|
| | | 18 Quantum dot | 40 Melamine | 50 Silica | 80 Melamine | 158 Melamine | 280 Silica | 320 Melamine |
| The number of fluorescent particles per field | Example 2 | 50 | 1800 | 1700 | 1800 | 1500 | 900 | 190 |
| | Comparative Example 2 | 30 | 400 | 500 | 400 | 300 | 320 | 140 |

Table 2 shows that the number of bright spots calculated by the process of the present invention (Example 2) was always larger and was closer to the true number than that calculated by the conventional process (Comparative Example 2). In particular, in the count of fluorescent particles having average particle sizes of 40 to 280 nm, the calculated number of bright spots was double or more of that in the conventional process, exhibiting the significant effectiveness of the process of the present invention.

Tissue samples stained with Staining reagent (b) derived from a quantum dot having an average particle size of 18 nm had weak fluorescent signals, which were readily buried in autofluorescent noises from the tissue samples. For this expressed in these cultured cells were determined with an ELISA kit (Human HER2 (Total) kit, No. KH00701) made by Invitrogen Corporation.

Figure 12:
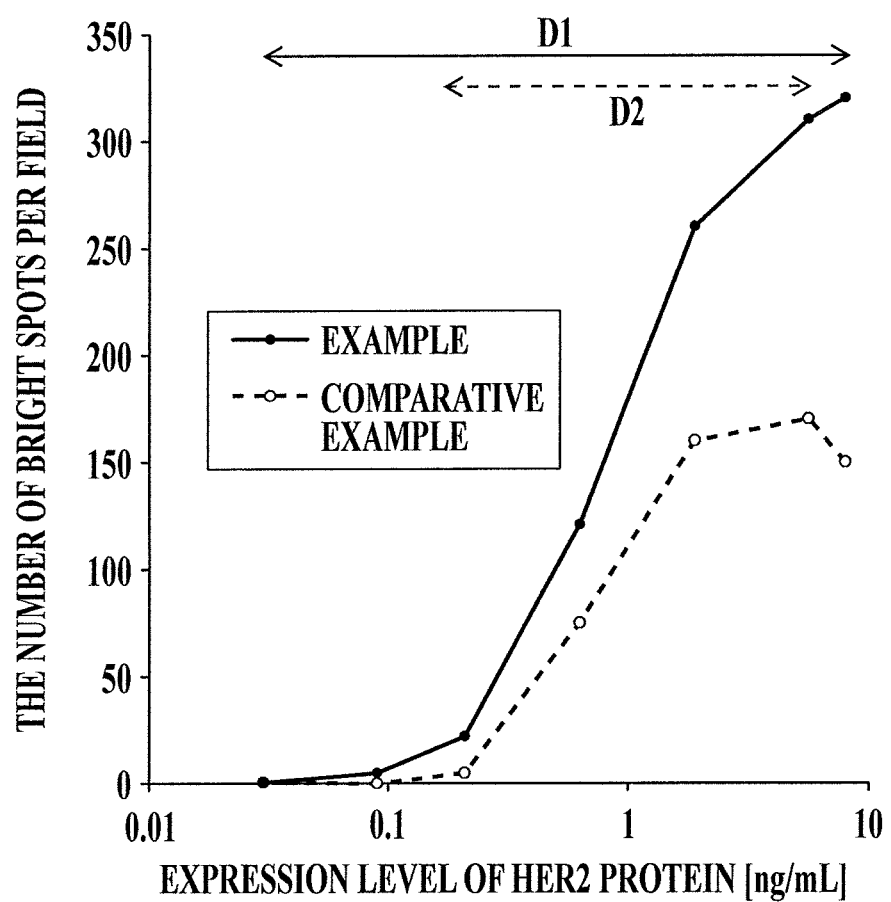
FIG. 12 is a diagram illustrating the numbers of bright spots relative to the expression level of HER2 protein, determined by the method of the present invention and a conventional method.

FIG. 12 is a graph of the number of bright spots per field plotted against the expression level of the HER2 protein in the seven cultured cells stained with Staining reagent (a) derived from fluorescent substance-encapsulating melamine nanoparticles having an average particle size of 80 nm. The number of bright spots per field is counted by the process (E-1) of the present invention and the conventional process (E-2).

The range of the expression level in which the counted number of bright spots per field monotonously increases as the expression level increases is called a dynamic range. For example, in FIG. 12, the dynamic range represents the range of a positive slope in the expression level of the HER2 protein. A broader dynamic range is advantageous because a change in expression level can be detected in a broader range of expression level.

FIG. 12 shows that the dynamic range of Staining reagent (a) derived from fluorescent substance-encapsulating melamine nanoparticles having an average particle size of 80 nm was 0.03 to 7.98 ng/mL (FIG. 12, D1) in the process of the present invention and was 0.21 to 5.58 ng/mL (FIG. 12, D2) in the conventional process.

Table 3 shows the dynamic ranges at a variety of average particle sizes and materials of the fluorescent particles in the count by the process (E-1) of the present invention and the conventional process (E-2).

TABLE 3

| | | Diameter of fluorescent particle[nm], Material | | | | |
|---|---|---|---|---|---|---|
| | | 18 Quantum dot | 40 Melamine | 50 Silica | 80 Melamine | 158 Melamine |
| Dynamic range [ng/ml] | Example 3 | 0.4-3.13 | 0.02-8.25 | 0.05-6.38 | 0.03-7.98 | 0.07-6.85 |
| | Comparative Example 3 | 0.4-3.13 | 0.18-5.24 | 0.12-5.46 | 0.21-5.58 | 0.12-5.46 |

Table 3 shows that tissue samples stained with Staining reagent (a) derived from fluorescent particles having average particle sizes of 40 to 158 nm exhibited broader dynamic ranges in the process of the present invention (Example 3) than in the conventional process (Comparative Example 3). In the method of the present invention, the dynamic range particularly remarkably expanded to a lower expression level of the HER2 protein.

The tissue samples stained with Staining reagent (b) derived from a quantum dot having an average particle size of 18 nm exhibited the same dynamic range in the process of the present invention and the conventional process.

<Experimental Result 4>

Human breast tissue samples were immunostained with Staining reagent (a). The tissue samples used were tissue array slides (CB-A712) made by Cosmo Bio Co., Ltd. The tissue samples visualized by DAB staining of HER2 antibodies bound to HER2 antigen sites were observed, and were classified into four groups of expression levels of the HER2 protein from score 0 (low expression) to score 3 (high expression).

The number of bright spots per cell was counted by the process (E-1) of the present invention and the conventional process (E-2). The results are shown in Table 4.

Table 4 shows that the method of the present invention (Example 4) leads to a significant increase in the number of bright spots as the score increased, indicating high sensitivity in detection of a change in expression level of the HER2 protein. In particular, in the tissue samples of Experimental result 2 stained with Staining reagents (a) derived from fluorescent particles having average particle sizes of 40 to 80 nm in which a particularly large number of bright spots (1700 to 1800 bright spots/field) were counted, the number of bright spots counted in the tissue samples of score 1 was three times at maximum the number of bright spots counted in the tissue samples of score 0 in the conventional method (Comparative Example 4). In contrast, in the process of the present invention, the number of bright spots counted at the tissue samples of score 1 was 12 to 21 times the number of bright spots counted at the tissue samples of score 0, and the sensitivity was significantly enhanced in detection of the HER2 protein at low expression level in particular.

The number of bright spots counted by the process of the present invention was small on the whole in the tissue samples stained with Staining reagent (a) derived from fluorescent particles having an average particle size of 158 nm. This result may come from slightly low binding ability of fluorescent particles having a large particle size.

The bright spots were observed immediately after the staining and after one month in the tissue samples stained with fluorescent particles derived from melamine and silica. Clear bright spots were observed after one month in images of the tissue samples stained with fluorescent particles derived from melamine. In contrast, images of the tissue samples stained with phosphor-integrated nanoparticles derived from silica were blurred after one month. It is inferred that the encapsulated dye was released from particles rather than being held in the particles.

In Experimental results 2 to 4, among the fluorescent particles having substantially the same average particle size, a larger number of bright spots were counted and a broader dynamic range was exhibited in the fluorescent particles

TABLE 4

| | | | Diameter of fluorescent particle[nm], Material | | | | |
|---|---|---|---|---|---|---|---|
| | | | 18 Quantum dot | 40 Melamine | 50 Silica | 80 Melamine | 158 Melamine |
| The number of bright spots per cell | Example 4 | Score 0 | 0 | 2 | 3 | 3 | 4 |
| | | Score 1 | 0 | 42 | 35 | 40 | 10 |
| | | Score 2 | 4 | 78 | 67 | 70 | 21 |
| | | Score 3 | 42 | 253 | 231 | 194 | 55 |
| | Comparative Example 4 | Score 0 | 0 | 2 | 3 | 3 | 4 |
| | | Score 1 | 0 | 6 | 8 | 7 | 4 |
| | | Score 2 | 4 | 13 | 12 | 14 | 7 |
| | | Score 3 | 23 | 35 | 43 | 32 | 15 | derived from melamine than in the fluorescent particles derived from silica. The results may come from a difference in stability between these fluorescent particles. Preferred are fluorescent particles derived from melamine in consideration of long-term storage and the stability after the staining step.

In conclusion, the quantitative determination method of a biological substance according to the present invention reduces errors in the average luminance per fluorescent particle, resulting in accurate determination of the number of specific biological substances in a sample.

The quantitative determination method of a biological substance according to the present invention also provides an expanded dynamic range that can detect a change in low expression level of a biological substance. It is believed that such an expanded dynamic range provided by the method according to the present invention can detect a slight increase in a biological substance due to a disease, such as cancer, from the normal expression level during quantitative determination of the biological substance, and enhances the accuracy in initial diagnosis of disease.

The quantitative determination method of a biological substance according to the present invention is particularly suitable for detection of the HER2 protein exhibiting high correlation between a pathological change and the expression level per cell because of the expanded dynamic range for recognizing a change in expression level of a biological substance. Any biological substance other than the HER2 protein or Ki67 protein also can be quantitatively determined by the method according to the present invention. Moreover, a feature quantity quantitatively indicating the expression level of a biological substance can be provided to medical doctors according to the type of the pathological change of interest (cancer) by varying the biological substance recognizing site used to take fluorescent images according to the pathological change.

INDUSTRIAL APPLICABILITY

The present invention provides accurate count of the number of specific biological substances in a sample, and can be particularly suitably used in generation of highly accurate information for pathological diagnosis.

DESCRIPTION OF SYMBOLS 1A microscopic imaging device
2A image processing device
3A cable
21 control unit
22 operation unit
23 display unit
24 communication interface
25 storage unit
26 bus
100 pathological diagnosis supporting system

The invention claimed is:

1. A quantitative determination method of a biological substance in a sample stained with a staining reagent comprising fluorescent particles each encapsulating a fluorescent substance and binding to a biological substance recognizing site, the method comprising:
  an inputting step of inputting a fluorescent image obtained by photographing the sample,
  a first calculating step of extracting a predetermined region from the fluorescent image to calculate an integrated luminance of the predetermined region, and
  a second calculating step of counting the number of fluorescent particles contained in the predetermined region from the integrated luminance and the average luminance per fluorescent particle,
  wherein the average luminance per fluorescent particle is calculated in advance from a correlation between the number of fluorescent particles actually counted from an image taken with an electron microscopic and the luminance derived from fluorescent light from the fluorescent particles and calculated from a fluorescent image of a region identical to the region taken in the image taken with an electron microscopic from which the number of fluorescent particles is actually counted.

2. The quantitative determination method of a biological substance according to claim 1,
  wherein calculation of the average luminance per fluorescent particle comprises:
  a step of extracting bright spot regions from a fluorescent image obtained by photographing the fluorescent particles, the bright spot regions being derived from fluorescent light from the fluorescent particles,
  a step of calculating a luminance of bright spots through integration of luminances of the bright spot regions,
  a step of counting the number of fluorescent particles contained in each of the bright spot regions with a scanning electron microscope, and
  a step of calculating the average luminance from a correlation between the luminance of bright spots and the number of fluorescent particles contained in each of the bright spot regions.

3. The quantitative determination method of a biological substance according to claim 1,
  wherein the fluorescent particles have an average particle size of 40 nm or more and 280 nm or less.

4. The quantitative determination method of a biological substance according to claim 1,
  wherein the fluorescent particles comprise melamine.

5. The quantitative determination method of a biological substance according to claim 1,
  wherein the biological substance is a HER2 protein or Ki67 protein.

6. The quantitative determination method of a biological substance according to claim 1, further comprising a step of calibrating the average luminance per fluorescent particle.

7. An image processing device for quantitative determination of a biological substance from an image obtained from a sample stained with a staining reagent comprising fluorescent particles each encapsulating a fluorescent substance and binding to a biological substance recognizing site, the device comprising:
  an input unit inputting a fluorescent image obtained by photographing the sample,
  a first calculating unit of extracting a predetermined region from the fluorescent image to calculate an integrated luminance of the predetermined region, and
  a second calculating unit of counting the number of fluorescent particles contained in the predetermined region from the integrated luminance and the average luminance per fluorescent particle,
  wherein the average luminance per fluorescent particle is calculated in advance from a correlation between the number of fluorescent particles actually counted from an image taken with an electron microscopic and the luminance derived from fluorescent light from the fluorescent particles and calculated from a fluorescent image of a region identical to the region taken in the image taken with an electron microscopic from which the number of fluorescent particles is actually counted.

8. A pathological diagnosis support system, comprising:
the image processing device according to claim 7, and
an imaging device acquiring the fluorescent image to be used in the image processing device.

9. A quantitative determination method of a biological substance in a sample stained with a staining reagent comprising fluorescent particles each encapsulating a fluorescent substance and binding to a biological substance recognizing site, the method comprising:
   an inputting step of inputting a fluorescent image obtained by photographing the sample,
   a first calculating step of extracting a predetermined region from the fluorescent image to calculate an integrated luminance of the predetermined region, and
   a second calculating step of counting the number of fluorescent particles contained in the predetermined region from the integrated luminance and the average luminance per fluorescent particle,
   wherein the average luminance per fluorescent particle is calculated in advance from a correlation between the number of fluorescent particles actually counted from an image taken with a scanning electron microscopic and the luminance derived from fluorescent light from the fluorescent particles and calculated from a fluorescent image of a region identical to the region taken in the image taken with a scanning electron microscopic from which the number of fluorescent particles is actually counted.

10. The quantitative determination method of a biological substance according to claim 9,
    wherein calculation of the average luminance per fluorescent particle comprises:
    a step of extracting bright spot regions from a fluorescent image obtained by photographing the fluorescent particles, the bright spot regions being derived from fluorescent light from the fluorescent particles,
    a step of calculating a luminance of bright spots through integration of luminances of the bright spot regions,
    a step of counting the number of fluorescent particles contained in each of the bright spot regions with a scanning electron microscope, and
    a step of calculating the average luminance from a correlation between the luminance of bright spots and the number of fluorescent particles contained in each of the bright spot regions.

11. The quantitative determination method of a biological substance according to claim 9,
    wherein the fluorescent particles have an average particle size of 40 nm or more and 280 nm or less.

12. The quantitative determination method of a biological substance according to claim 9,
    wherein the fluorescent particles comprise melamine.

13. The quantitative determination method of a biological substance according to claim 9,
    wherein the biological substance is a HER2 protein or Ki67 protein.

14. The quantitative determination method of a biological substance according to claim 9, further comprising a step of calibrating the average luminance per fluorescent particle.

15. An image processing device for quantitative determination of a biological substance from an image obtained from a sample stained with a staining reagent comprising fluorescent particles each encapsulating a fluorescent substance and binding to a biological substance recognizing site, the device comprising:
    an input unit inputting a fluorescent image obtained by photographing the sample,
    a first calculating unit of extracting a predetermined region from the fluorescent image to calculate an integrated luminance of the predetermined region, and
    a second calculating unit of counting the number of fluorescent particles contained in the predetermined region from the integrated luminance and the average luminance per fluorescent particle,
    wherein the average luminance per fluorescent particle is calculated in advance from a correlation between the number of fluorescent particles actually counted from an image taken with a scanning electron microscopic and the luminance derived from fluorescent light from the fluorescent particles and calculated from a fluorescent image of a region identical to the region taken in the image taken with a scanning electron microscopic from which the number of fluorescent particles is actually counted.

16. A pathological diagnosis support system, comprising:
the image processing device according to claim 15, and
an imaging device acquiring the fluorescent image to be used in the image processing device.

* * * * *